United States Patent
Fang et al.

(10) Patent No.: US 11,634,496 B2
(45) Date of Patent: Apr. 25, 2023

(54) C-MET AGONISTIC ANTIBODY AND USE THEREOF

(71) Applicant: TONGJI UNIVERSITY SUZHOU INSTITUTE BIOMEDICAL RESEARCH CENTER, Jiangsu (CN)

(72) Inventors: Jianmin Fang, Jiangsu (CN); Ming Jiang, Shanghai (CN); Yanxin Yin, Shanghai (CN); Jia Guo, Jiangsu (CN); Lihua Yu, Jiangsu (CN)

(73) Assignee: TONGJI UNIVERSITY SUZHOU INSTITUTE BIOMEDICAL RESEARCH CENTER, Jiangsu (CN)

( * ) Notice: Subject to any disclaimer, the term of this patent is extended or adjusted under 35 U.S.C. 154(b) by 2 days.

(21) Appl. No.: 16/763,201

(22) PCT Filed: Oct. 31, 2018

(86) PCT No.: PCT/CN2018/112874
§ 371 (c)(1),
(2) Date: May 11, 2020

(87) PCT Pub. No.: WO2019/091306
PCT Pub. Date: May 16, 2019

(65) Prior Publication Data
US 2021/0087277 A1     Mar. 25, 2021

(30) Foreign Application Priority Data

Nov. 13, 2017 (CN) .......................... 201711116927.1

(51) Int. Cl.
| | |
|---|---|
| C07K 16/28 | (2006.01) |
| A61K 39/395 | (2006.01) |
| A61K 39/00 | (2006.01) |
| A61P 9/10 | (2006.01) |
| A61K 45/06 | (2006.01) |
| A61K 31/337 | (2006.01) |

(52) U.S. Cl.
CPC ........ *C07K 16/2863* (2013.01); *A61K 31/337* (2013.01); *A61K 39/39541* (2013.01); *A61K 45/06* (2013.01); *A61P 9/10* (2018.01); *A61K 2039/505* (2013.01); *C07K 2317/24* (2013.01); *C07K 2317/565* (2013.01); *C07K 2317/75* (2013.01)

(58) Field of Classification Search
None
See application file for complete search history.

(56) References Cited

U.S. PATENT DOCUMENTS

| | | |
|---|---|---|
| 2010/0129369 A1 | 5/2010 | Davies et al. |
| 2011/0239316 A1 | 9/2011 | Goetsch et al. |
| 2012/0148607 A1 | 6/2012 | Hultberg et al. |

FOREIGN PATENT DOCUMENTS

| | | | |
|---|---|---|---|
| CN | 102216333 A | | 10/2011 |
| CN | 102227446 A | | 10/2011 |
| CN | 103562223 A | | 2/2014 |
| WO | WO 2011/015652 A1 | | 2/2011 |
| WO | WO 2014/153117 A2 | | 9/2014 |
| WO | WO 2017/135791 A1 | | 8/2017 |
| WO | WO 2022/048521 | * | 3/2022 |

OTHER PUBLICATIONS

Yang, Y. et al. "Research Progress on the Mechanism of Vascular Endothelial Cells in Tissue Ischemia-Reperfusion Injury" *Beijing Journal of Stomatology*, vol. 25, No. (05), pp. 294-296, Oct. 31, 2017.
Rao, K.S. et al. "Human Epicardial Cell-Conditioned Medium Contains HGF/IgG Complexes that Phosphorylate RYK and Protect Against Vascular Injury" *Cardiovascular Research*, vol. 107, No. 2, pp. 277-286, May 29, 2015.
Vasuri, F. et al. "Biochemical and Immunomorphological Evaluation of Hepatocyte Growth Factor and c-Met Pathway in Patients with Critical Limb Ischemia" *European Society for Vascular Surgery*, vol. 48, No. 4, pp. 430-437, Jun. 16, 2014.
Nakamura, T. et al. "Myocardial Protection from Ischemia/Reperfusion Injury Endogenous and Exogenous HGF" *The Journal of Clinical Investigation*, vol. 106, No. 12, pp. 1511-1519, Dec. 31, 2000.
International Search Report in International Application No. PCT/CN2018/112874 dated Jan. 30, 2019.

* cited by examiner

*Primary Examiner* — Marianne P Allen
(74) *Attorney, Agent, or Firm* — Knobbe, Martens, Olson & Bear LLP

(57) ABSTRACT

A method for treating or preventing vascular endothelial cell injured diseases, especially cerebral infarctions or myocardial infarctions, by administering a c-MET agonist antibody to a subject in need thereof, and specific c-MET agonist antibodies.

6 Claims, 14 Drawing Sheets

Specification includes a Sequence Listing.

a b a b

SEQUENCE LISTING

<160> NUMBER OF SEQ ID NOS: 14

<210> SEQ ID NO 1
<211> LENGTH: 44
<212> TYPE: DNA
<213> ORGANISM: Artificial sequence
<220> FEATURE:
<223> OTHER INFORMATION: Primer P1

<400> SEQUENCE: 1
tataccggtc gccaccatga aggccccgc tgtgcttgca cctg          44

<210> SEQ ID NO 2
<211> LENGTH: 56
<212> TYPE: DNA
<213> ORGANISM: Artificial sequence
<220> FEATURE:
<223> OTHER INFORMATION: Primer P1

<400> SEQUENCE: 2
cgcgtcgacc tagtgatggt gatgatggtg tgtgaaattc tgatctggtt gacata          56

<210> SEQ ID NO 3
<211> LENGTH: 2796
<212> TYPE: DNA
<213> ORGANISM: Homo sapiens

<400> SEQUENCE: 3
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg aacacccag attgtttccc atgtcaggac    300
tgcagcagca agccaattt atcaggaggt gtttggaaag ataacatcaa catggctcta    360
gttgtcgaca cctactatga tgatcaactc attagctgtg gcagcgtcaa cagagggacc    420
tgccagcgac atgtcttcc ccacaatcat actgctgaca cagtcgga ggttcactgc    480 atattctccc cacagataga agagcccagc cagtgtcctg actgtgtggt gagcgccctg    540
ggagccaaag tcctttcatc tgtaaaggac cggttcatca cttctttgt aggcaatacc    600 ataaattctt cttatttccc agatcatcca ttgcattcga tatcagtgag aaggctaaag    660
gaaacgaaag atggttttat gttttgacg gaccagtcct acattgatgt ttacctgag    720 ttcagagatt cttaccccat taagtatgtc catgcctttg aaagcaacaa ttttatttac    780

-continued

| | |
|---|---|
| ttcttgacgg tccaaaggga aactctagat gctcagactt tcacacaag aataatcagg | 840 |
| ttctgttcca taaactctgg attgcattcc tacatggaaa tgcctctgga gtgtattctc | 900 |
| acagaaaaga gaaaaagag atccacaaag aaggaagtgt taatatact tcaggctgcg | 960 |
| tatgtcagca agcctggggc ccagcttgct agacaaatag gagccagcct gaatgatgac | 1020 |
| attcttttcg gggtgttcgc acaaagcaag ccagattctg ccgaaccaat ggatcgatct | 1080 |
| gccatgtgtg cattccctat caaatatgtc aacgacttct tcaacaagat cgtcaacaaa | 1140 |
| aacaatgtga gatgtctcca gcatttttac ggacccaatc atgagcactg ctttaatagg | 1200 |
| acacttctga gaaattcatc aggctgtgaa gcgcgccgtg atgaatatcg aacagagttt | 1260 |
| accacagctt tgcagcgcgt tgacttattc atgggtcaat tcagcgaagt cctcttaaca | 1320 |
| tctatatcca ccttcattaa aggagaccct accatagcta atcttgggac atcagagggt | 1380 |
| cgcttcatgc aggttgtggt ttctcgatca ggaccatcaa cccctcatgt gaattttctc | 1440 |
| ctggactccc atccagtgtc tccagaagtg attgtggagc atacattaaa ccaaaatggc | 1500 |
| tacacactgg ttatcactgg gaagaagatc acgaagatcc cattgaatgg cttgggctgc | 1560 |
| agacatttcc agtcctgcag tcaatgcctc tctgccccac cctttgttca gtgtggctgg | 1620 |
| tgccacgaca atgtgtgcg atcggaggaa tgcctgagcg ggacatggac tcaacagatc | 1680 |
| tgtctgcctg caatctacaa ggttttccca aatagtgcac cccttgaagg agggacaagg | 1740 |
| ctgaccatat gtggctggga ctttggattt cggaggaata taaatttga tttaaagaaa | 1800 |
| actagagttc tccttggaaa tgagagctgc accttgactt taagtgagag cacgatgaat | 1860 |
| acattgaaat gcacagttgg tcctgccatg aataagcatt tcaatatgtc cataattatt | 1920 |
| tcaaatggcc acgggacaac acaatacagt acattctcct atgtggatcc tgtaataaca | 1980 |
| agtatttcgc cgaaatacgg tcctatggct ggtggcactt tacttacttt aactggaaat | 2040 |
| tacctaaaca gtgggaattc tagacacatt tcaattggtg aaaaacatg tactttaaaa | 2100 |
| agtgtgtcaa acagtattct tgaatgttat accccagccc aaaccatttc aactgagttt | 2160 |
| gctgttaaat tgaaaattga cttagccaac cgagagacaa gcatcttcag ttaccgtgaa | 2220 |
| gatcccattg tctatgaaat tcatccaacc aaatctttta ttagtggtgg agcacaata | 2280 |
| acaggtgttg ggaaaaacct gaattcagtt agtgtcccga gaatggtcat aaatgtgcat | 2340 |
| gaagcaggaa ggaactttac agtggcatgt caacatcgct ctaattcaga gataatctgt | 2400 |
| tgtaccactc cttccctgca acagctgaat ctgcaactcc cctgaaaaac caaagccttt | 2460 |
| ttcatgttag atgggatcct ttccaaatac tttgatctca tttatgtaca taatcctgtg | 2520 |
| tttaagcctt ttgaaaagcc agtgatgatc tcaatgggca atgaaaatgt actggaaatt | 2580 |
| aagggaaatg atattgaccc tgaagcagtt aaaggtgaag tgttaaaagt tggaaataag | 2640 |
| agctgtgaga atatacactt acattctgaa gccgttttat gcacggtccc caatgacctg | 2700 |
| ctgaaattga acagcgagct aaatatagag tggaagcaag caatttcttc aaccgtcctt | 2760 |
| ggaaaagtaa tagttcaacc agatcagaat ttcaca | 2796 |

<210> SEQ ID NO 4
<211> LENGTH: 932
<212> TYPE: PRT
<213> ORGANISM: Homo sapiens

<400> SEQUENCE: 4

Met Lys Ala Pro Ala Val Leu Ala Pro Gly Ile Leu Val Leu Leu Phe
1               5                   10                  15

```
Thr Leu Val Gln Arg Ser Asn Gly Glu Cys Lys Glu Ala Leu Ala Lys
             20                  25                  30
Ser Glu Met Asn Val Asn Met Lys Tyr Gln Leu Pro Asn Phe Thr Ala
         35                  40                  45
Glu Thr Pro Ile Gln Asn Val Ile Leu His Glu His Ile Phe Leu
     50                  55                  60
Gly Ala Thr Asn Tyr Ile Tyr Val Leu Asn Glu Glu Asp Leu Gln Lys
65                  70                  75                  80
Val Ala Glu Tyr Lys Thr Gly Pro Val Leu Glu His Pro Asp Cys Phe
                 85                  90                  95
Pro Cys Gln Asp Cys Ser Ser Lys Ala Asn Leu Ser Gly Gly Val Trp
             100                 105                 110
Lys Asp Asn Ile Asn Met Ala Leu Val Val Asp Thr Tyr Tyr Asp Asp
         115                 120                 125
Gln Leu Ile Ser Cys Gly Ser Val Asn Arg Gly Thr Cys Gln Arg His
     130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                 165                 170                 175
Val Ser Ala Leu Gly Ala Lys Val Leu Ser Ser Val Lys Asp Arg Phe
             180                 185                 190
Ile Asn Phe Phe Val Gly Asn Thr Ile Asn Ser Ser Tyr Phe Pro Asp
         195                 200                 205
His Pro Leu His Ser Ile Ser Val Arg Arg Leu Lys Glu Thr Lys Asp
     210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                 245                 250                 255
Asn Phe Ile Tyr Phe Leu Thr Val Gln Arg Glu Thr Leu Asp Ala Gln
             260                 265                 270
Thr Phe His Thr Arg Ile Ile Arg Phe Cys Ser Ile Asn Ser Gly Leu
         275                 280                 285
His Ser Tyr Met Glu Met Pro Leu Glu Cys Ile Leu Thr Glu Lys Arg
     290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                 325                 330                 335
Leu Asn Asp Asp Ile Leu Phe Gly Val Phe Ala Gln Ser Lys Pro Asp
             340                 345                 350
Ser Ala Glu Pro Met Asp Arg Ser Ala Met Cys Ala Phe Pro Ile Lys
         355                 360                 365
Tyr Val Asn Asp Phe Phe Asn Lys Ile Val Asn Lys Asn Asn Val Arg
     370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                 405                 410                 415
Arg Thr Glu Phe Thr Thr Ala Leu Gln Arg Val Asp Leu Phe Met Gly
             420                 425                 430
Gln Phe Ser Glu Val Leu Leu Thr Ser Ile Ser Thr Phe Ile Lys Gly
```

```
                435                 440                 445
Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                    485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                    645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
                770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                    805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
                850                 855                 860
```

```
Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
        900                 905                 910

Gln Ala Ile Ser Ser Thr Val Leu Gly Lys Val Ile Val Gln Pro Asp
            915                 920                 925

Gln Asn Phe Thr
    930

<210> SEQ ID NO 5
<211> LENGTH: 20
<212> TYPE: DNA
<213> ORGANISM: Artificial  sequence
<220> FEATURE:
<223> OTHER INFORMATION: Primer. s is g or c; r is a or g; m is a or c.

<400> SEQUENCE: 5
sargtrmagc tgmagsagtc                                             20

<210> SEQ ID NO 6
<211> LENGTH: 27
<212> TYPE: DNA
<213> ORGANISM: Artificial sequence
<220> FEATURE:
<223> OTHER INFORMATION: Primer

<400> SEQUENCE: 6
aattttcttg tccaccttgg tgctgct                                     27

<210> SEQ ID NO 7
<211> LENGTH: 21
<212> TYPE: DNA
<213> ORGANISM: Artificial sequence
<220> FEATURE:
<223> OTHER INFORMATION: Primer. y is c or t; d is g, a or t; m is a or
      c; s is g or c; r is a or g; w is a or t.

<400> SEQUENCE: 7
gayattgtdm tsacmcarwc t                                           21

<210> SEQ ID NO 8
<211> LENGTH: 26
<212> TYPE: DNA
<213> ORGANISM: Artificial sequence
<220> FEATURE:
<223> OTHER INFORMATION: Primer

<400> SEQUENCE: 8
ggatacagtt ggtgcagcat cagccc                                      26

<210> SEQ ID NO 9
<211> LENGTH: 8
<212> TYPE: PRT
<213> ORGANISM: Artificial sequence
<220> FEATURE:
<223> OTHER INFORMATION: Heavy chain CDR1

<400> SEQUENCE: 9

Gly Tyr Ser Phe Thr Ser Tyr Trp
1               5
```

```
<210> SEQ ID NO 10
<211> LENGTH: 8
<212> TYPE: PRT
<213> ORGANISM: Artificial sequence
<220> FEATURE:
<223> OTHER INFORMATION: Heavy chain CDR2

<400> SEQUENCE: 10

Ile Asp Pro Ser Asp Ser Glu Ser
1               5

<210> SEQ ID NO 11
<211> LENGTH: 15
<212> TYPE: PRT
<213> ORGANISM: Artificial sequence
<220> FEATURE:
<223> OTHER INFORMATION: Heavy chain CDR3

<400> SEQUENCE: 11

Ala Arg Ser Gly Tyr His Gly Thr Ser Tyr Trp Tyr Phe Asp Val
1               5                   10                  15

<210> SEQ ID NO 12
<211> LENGTH: 11
<212> TYPE: PRT
<213> ORGANISM: Artificial  sequence
<220> FEATURE:
<223> OTHER INFORMATION: Light chain CDR1

<400> SEQUENCE: 12

Lys Ser Leu Leu His Ser Asp Gly Ile Thr Tyr
1               5                   10

<210> SEQ ID NO 13
<211> LENGTH: 3
<212> TYPE: PRT
<213> ORGANISM: Artificial sequence
<220> FEATURE:
<223> OTHER INFORMATION: Light chain CDR2

<400> SEQUENCE: 13

Gln Met Ser
1

<210> SEQ ID NO 14
<211> LENGTH: 9
<212> TYPE: PRT
<213> ORGANISM: Artificial sequence
<220> FEATURE:
<223> OTHER INFORMATION: Light chain CDR3

<400> SEQUENCE: 14

Ala Gln Asn Leu Glu Leu Pro Pro Thr
1               5
```

C-MET AGONISTIC ANTIBODY AND USE THEREOF

SEQUENCE LISTING STATEMENT

The present application contains a Sequence Listing, which is being submitted via EFS-Web on even date herewith. The Sequence Listing is submitted in a file entitled "Sequence_Listing_UTLN026-001APC.txt," which was created on May 11, 2020, and is 14,308 bytes in size. This Sequence Listing is hereby incorporated by reference.

CROSS-REFERENCE TO RELATED APPLICATIONS

The present application claims the priority of Chinese Patent Application No. 201711116927.1 filed on Nov. 13, 2017 at the Chinese Patent Office, entitled "C-MET AGONISTIC ANTIBODY AND USE THEREOF", which is incorporated herein by reference in its entirety.

FIELD

The present invention relates to use of a c-MET agonist antibody in the manufacture of a medicament for treating or preventing a disease caused by vascular endothelial cell injury (including, for example, a ischemic disease or a disease caused by blood-brain barrier injury), and especially cerebral infarction or myocardial infarction. The present invention also relates to a c-MET agonist antibody.

BACKGROUND

After restoring blood perfusion, the ischemic tissue would undergo a pathological process termed as ischemia-reperfusion injury (IR) wherein the metabolic dysfunction and structural destruction of tissues and cells are further aggravated. Clinically, IR is involved in all the ischemia and hypoxia of organs and tissues due to various reasons during treatment and recovery, such as organ transplantation, stroke, traumatic shock, myocardial infarction, lower limb ischemia. Vascular endothelial cells are monolayer cells attached to the inner wall of microvessels. They constitute a barrier between blood vessels and tissues, and are a hub for regulating tissue and cell metabolism by secreting various biologically active substances to regulate vascular tension, coagulation-fibrinolysis balance, and inflammatory immune response Cerebrovascular endothelial cells are an important component of the blood-brain barrier, and their injury would cause many secondary pathological processes. Recent studies have found that vascular endothelial cells are an important site where IR occurs, and thus the protection of microvascular endothelial cells is the key to the prevention and treatment of IR.

Hepatocyte growth factor (HGF) and its receptor c-MET have been shown to be effective targets for protecting vascular endothelial cells. The binding of HGF to the receptor c-MET can activate a related signaling pathway to specifically promote and maintain endothelial cell proliferation and function, promote neovascularization and thereby promote angiogenesis forming collateral circulation. Therefore, HGF/c-MET is widely used as a target for the protection and repair of blood vessels. Chinese Patent Application Publication No. CN101925362A discloses use of a composition comprising two or more isoforms of HGF in the manufacture of a medicament for promoting the growth of endothelial cells in a blood vessel, including a method for increasing the perfusion or blood vessel density in myocardium of ischemic heart tissue, enhancing endothelial repair or treating injured or diseased blood vessels in a subject.

At present, there is a still huge obstacle for the method for in vivo and clinical application of HGF. The serum half-life of HGF is extremely short, less than 5 minutes, which greatly limits the application of recombinant HGF. For this reason, for studying its potential clinical application value, a usually adopted strategy is introducing the HGF gene directly into the body through viral vectors, so that it can be endogenously and continuously expressed in the ischemic site. For example, Chinese Patent Application Publication No. CN1502368A discloses the application of a recombinant adenovirus carrying HGF gene in cerebral ischemia, including integrating human hepatocyte growth factor gene into a adenovirus vector through homologous recombination of intracellular plasmids to obtain the recombinant adenovirus, preparing a certain amount of virus particles, and establishing an animal model of cerebral ischemia and a suitable gene transfer method to observe the expression of the adenovirus in the brain. It is shown that human hepatocyte growth factor can reduce nerve cell death caused by cerebral ischemia. However, this method is still not satisfactory, including in terms of safety and therapeutic effect. Since it takes some time from the vector entering the cell to protein expression, immediate HGF expression would not be necessarily obtained, even if a vector injection method is used. However, rapid onset of action is particularly important for the treatment of ischemic diseases or ischemic injury of vascular endothelial cells (especially cerebral infarction or myocardial infarction). Therefore, there is still an urgent need in the prior art for a method to effectively promote the repair of vascular endothelial cell injury.

SUMMARY

The inventors have unexpectedly found that c-MET agonists can effectively promote the repair of vascular endothelial cell injury and therefore can be used to treat ischemic diseases and diseases caused by blood-brain barrier injury. C-MET belongs to receptor tyrosine kinases (RTKs) and consists of two monomers, each of which is a double-stranded protein linked by disulfide bonds. The activation of c-MET begins with the dimerization of the two monomers, and the tyrosine kinase region then undergoes autophosphorylation and signaling. By using the bivalent structure of an antibody, the two c-MET monomers can be simultaneously bound, making them spatially close to each other and undergoing dimerization, which in turn leads to autophosphorylation of tyrosine kinase, thereby achieving the purpose of activating c-MET.

The inventors have found that c-MET is an effective target for protecting vascular endothelial cells, and verified that a c-MET antibody has the role of activating the HGF/c-MET pathway. One purpose of the present invention is to provide a method for protecting vascular endothelial cells taking advantage of the beneficial properties of c-MET antibody and the use thereof for ischemic diseases and diseases caused by blood-brain barrier injury, as well as an antibody drug.

Therefore, in a first aspect of the present invention, use of a c-MET agonist in the manufacture of a medicament for the treatment or prevention of a disease caused by blood-brain barrier injury, especially an ischemic disease or ischemic injury of vascular endothelial cells is provided. Preferably, the c-MET agonist in the present invention is a c-MET agonist antibody. Those skilled in the art could understand that the c-MET agonist antibody can bind to an antigen, and this binding also reflects the binding of a ligand to a receptor, and would result in an enhanced activity or ability of the effector ligand.

Preferably, the ischemic disease is cerebral infarction or myocardial infarction. In preferred embodiments, the treatment or prevention of cerebral infarction is by reducing the permeability of the blood-brain barrier and/or by protecting and repairing cerebral blood vessels and/or by reducing the cerebral infarction size.

In the use of the present invention, the c-MET agonist may be a monoclonal antibody prepared by immunizing an animal with a c-MET antigen, or may be a c-MET full-length molecule, fusion protein, molecular fragment or polypeptide having immunogenicity. In a preferred embodiment, the c-MET agonist is obtained by screening a B lymphocyte antibody library, or can be obtained by screening a synthetic antibody library. In another preferred embodiment, the c-MET agonist is a genetically engineered antibody compound remaining an agonistic activity.

In the use of the present invention, the c-MET agonist may be a fully humanized antibody. Alternatively, the c-MET agonist may be an antibody with a humanized FR and/or Fc fragment.

In a particularly preferred embodiment, the c-MET agonist is an antibody molecule comprising a heavy chain and a light chain, and the heavy chain comprises at least one heavy chain variable region sequence selected from SEQ ID NO: 9, SEQ ID NO: 10, SEQ ID NO: 11, and a mutant sequence thereof; and the light chain comprises at least one light chain variable region sequence selected from SEQ ID NO: 12, SEQ ID NO: 13, SEQ ID NO: 14, and a mutant sequence thereof.

In the use of the present invention, the c-MET agonist can be an antibody-drug conjugate. The drug can be a pharmaceutically active ingredient known other than the above antibodies of the present invention, such as but not limited to IRF5 inhibitors, paclitaxel, lipid-lowering drugs or angiogenesis inhibitors.

In another aspect of the invention, provided is an antibody or functional fragment thereof capable of binding to c-MET, wherein the antibody comprises a heavy chain and a light chain, and wherein:

the heavy chain comprises at least one heavy chain variable region sequence selected from SEQ ID NO: 9, SEQ ID NO: 10, SEQ ID NO: 11, and a mutant sequence thereof; and the light chain comprises at least one light chain variable region sequence selected from SEQ ID NO: 12, SEQ ID NO: 13, SEQ ID NO: 14, and a mutant sequence thereof.

In yet another aspect of the present invention, provided is a pharmaceutical composition comprising the antibody or functional fragment thereof, and a pharmaceutically acceptable carrier.

The pharmaceutical composition of the present invention can be administered intravenously, intramuscularly, intradermally, intraperitoneally or subcutaneously, or orally. Particularly preferably, the pharmaceutical composition of the present invention is administered intravenously, and is an intravenous injection.

The pharmaceutical composition of the present invention may further comprise one or more pharmaceutically active compound for treatment or prevention of an ischemic disease or ischemic injury of vascular endothelial cells. The pharmaceutically active compound may be any compound known in the prior art for treatment or prevention of an ischemic disease or ischemic injury of vascular endothelial cells.

In yet another aspect of the present invention, provided is a method for protecting vascular endothelial cells subjected to ischemic injury, comprising administering a c-MET agonist to a subject. In a preferred aspect, the c-MET agonist is a c-MET antibody.

In a preferred embodiment, the c-MET antibody enables to promote c-MET dimerization, tyrosine phosphorylation, and activation of the c-MET signaling pathway.

In another preferred embodiment, the c-MET antibody is a monoclonal antibody prepared by immunizing an animal with c-MET antigen.

In another preferred embodiment, the c-MET antigen is a c-MET full-length molecule, fusion protein, molecular fragment or polypeptide having immunogenicity.

In another preferred embodiment, the c-MET antibody is obtained by screening a B lymphocyte antibody library.

In another preferred embodiment, the c-MET antibody is a genetically engineered antibody remaining an agonistic activity.

In another preferred embodiment, the c-MET antibody is an antibody with a humanized FR and/or Fc fragment.

In another preferred embodiment, the c-MET antibody is a fully humanized antibody.

In another preferred embodiment, the c-MET antibody is a polyclonal antibody with an agonistic activity.

In another preferred embodiment, the ischemic disease is cerebral infarction.

In another preferred embodiment, the composition is administered by intravenous injection.

In another preferred embodiment, the composition is used to protect and repair cerebral blood vessels.

In another preferred embodiment, the composition is used to reduce the permeability of the blood-brain barrier.

In another preferred embodiment, the composition is used to protect neurons.

In another preferred embodiment, the composition is used to reduce the cerebral infarction size.

In another preferred embodiment, the composition is used to maintain blood flow in an infarcted area.

In a third aspect of the present invention, provided is an antibody drug developed according to the method of the first aspect of the present invention for treating ischemic diseases.

In another preferred example, the antibody drug is produced by a hybridoma cell line.

In another preferred example, the antibody drug is an antigen-binding fragment thereof, which comprises at least one CDR region sequence selected from:

antibody heavy chain variable region (HCDR) sequence: SEQ ID NO: 9, SEQ ID NO: 10, SEQ ID NO: 11, and a mutant sequence thereof; and antibody light chain variable region (LCDR) sequence: SEQ ID NO: 12, SEQ ID NO: 13, SEQ ID NO: 14, and a mutant sequence thereof.

The present invention provides a pharmacologically feasible solution for treating ischemic diseases, as well as an alternative drug with a good efficacy.

BRIEF DESCRIPTION OF DRAWINGS

FIG. 11A is a photograph of cells in a control group at 0 hour after matrigel spreading, FIG. 11B is a photograph of cells in a group added with 1H9D6 with a concentration of 1 µg/ml at 0 hour after matrigel spreading, FIG. 11C is a photograph of cells in a control group at 72 hours after matrigel spreading, and FIG. 11D is a photograph of cells in a group added with 1H9D6 with a concentration of 1 µg/ml at 72 hours after matrigel spreading.

In FIG. 13a, the control group is a sample without oxygen-glucose deprivation treatment, the injured group is a sample with oxygen-glucose deprivation treatment and the treatment group is a sample with oxygen-glucose deprivation and added with an anti-c-MET humanized antibody, wherein the value is the concentration of the anti-c-MET humanized antibody in ng/ml. FIG. 13b shows the counts of apoptotic vascular endothelial cells (Bend.3) after oxygen-glucose deprivation treatment in the presence of the anti-c-MET humanized antibody.

Figure 1:
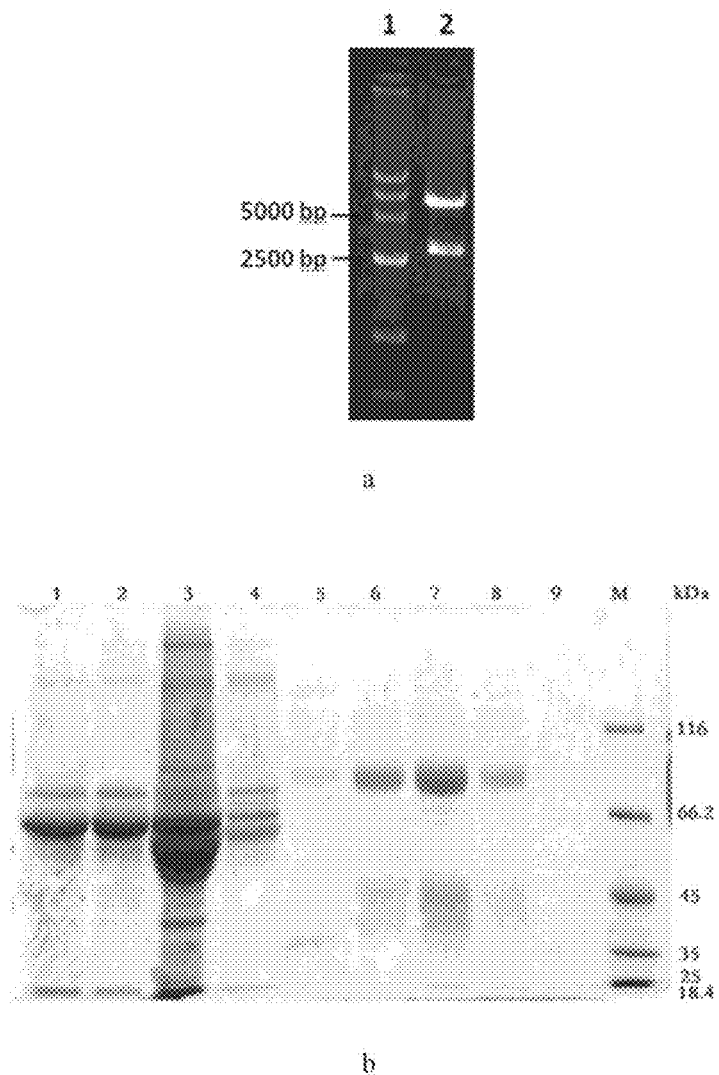
FIG. 1a is a diagram showing the enzymatic digestion of the lentiviral shuttle vector pRRL-CMV-ED in Example 1 of the present invention.
FIG. 1b is a diagram showing the detection result of the expression of a fusion protein with a key domain ED of c-MET in Example 1 of the present invention.

A detailed description of the experiments and results thereof involved in the above drawings of the present invention is as follows:

FIG. 1-a is an electrophoretogram showing the enzymatic digestion of the lentiviral shuttle vector pRRL-CMV-ED, in which lane 1 is a DNA marker, and lane 2 is a sample of the lentiviral shuttle vector pRRL-CMV-ED doubly enzymatically digested with Age I and Sal I. The result of enzymatic digestion shows a vector band of 7500 bp and a target gene band of 2700 bp, proving the successful construction of the lentiviral expression plasmid pRRL-CMV-ED of the ED fragment of the extracellular region of human MET; and FIG. 1-b is a diagram showing the detection result of the expression of a fusion protein with a key domain ED of MET. Lane 1: an expressed supernatant stock solution (1:5 dilution); lane 2: a column passing solution (1:5 dilution); lane 3: elution fractions with 20 mM Imidazole; lanes 4-5: elution fractions with 50 mM Imidazole; lanes 6-9: elution fractions with 200 mM Imidazole; M: a standard for protein molecular weight. The 105 KDa band in lanes 5-9 is consistent with the expected target band, proving the successful expression and purification of the fusion protein with the extracellular region ED of MET.

Figure 2:
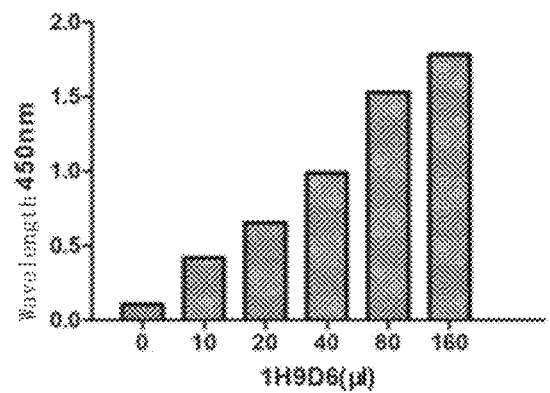
FIG. 2 is a diagram showing the results of detection of the binding ability of the supernatant of the hybridoma cell for c-MET antibody to the ED protein in Example 2 of the present invention.

FIG. 2 shows the results of detection of the binding ability of the supernatant of the hybridoma cell for an c-MET antibody to the ED protein in Example 2 of the present invention, in which the abscissa represents the loading volume of the hybridoma supernatant for an c-MET antibody in p, and the ordinate represents the absorbance at a wavelength of 450 nm. The results show that the supernatant of 1H9D6 hybridoma can specifically bind to the fusion protein with the extracellular region ED of MET, and the signal is increased as the volume added is increased.

Figure 3:
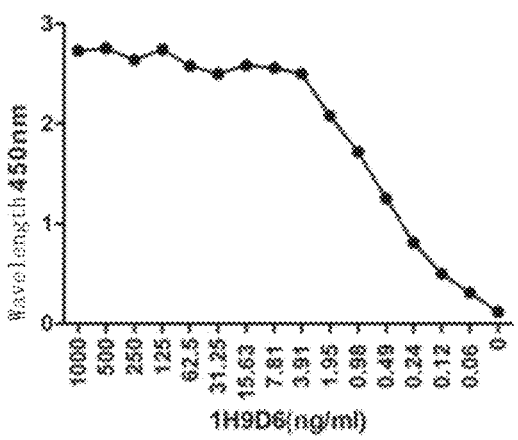
FIG. 3 is a diagram showing the binding ability of a c-MET monoclonal antibody to the extracellular region ED protein of c-MET in Example 3 of the present invention.

FIG. 3 shows the binding ability of a c-MET monoclonal antibody to the ED protein in the extracellular region of c-MET in Example 3 of the present invention, in which the abscissa represents the concentration of c-MET antibody in ng/ml, and the ordinate represents the absorbance at a wavelength of 450 nm. The results show that: the c-MET monoclonal antibody can specifically bind to the fusion protein with the extracellular region ED of c-MET, and the signal is increased as the concentration added is increased. Under this system condition, the minimum detection concentration of the c-MET monoclonal antibody is 0.06 ng/ml, proving that the c-MET monoclonal antibody 1H9D6 has a strong binding ability to the fusion protein with the extracellular region ED of MET.

Figure 4:
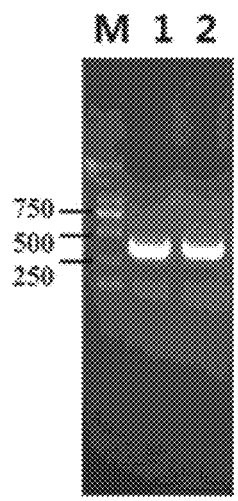
FIG. 4 is a diagram showing the calling of the genes of the heavy and light chain variable regions VH and VL of a c-MET antibody in Example 4 of the present invention.

FIG. 4 shows the calling of the genes of the heavy and light chain variable regions VH and VL of a c-MET antibody in Example 4 of the present invention, in which lane 1 is a DNA marker, lane 2 is a PCR product of the VH gene, and lane 3 is a PCR product of the VL gene. The electrophoresis shows the specific bands of the PCR products of mouse-derived VH and VL genes at about 351 and 336 bp, respectively, proving the successful calling of the mouse-derived VH and VL genes.

Figure 5:
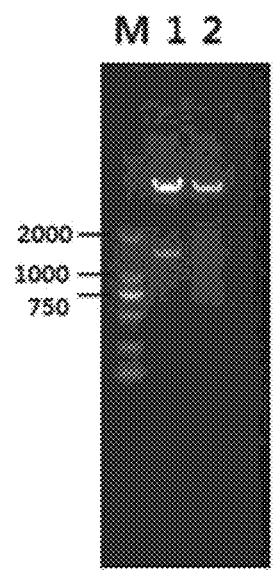
FIG. 5 is a diagram showing the enzymatic digestion of the lentiviral shuttle vectors pRRL-CMV-VH and pRRL-CMV-VL in Example 5 of the present invention.

FIG. 5 shows the enzymatic digestion of the lentiviral shuttle vectors pRRL-CMV-VH and pRRL-CMV-VL in Example 5 of the present invention, in which lane 1 is a DNA marker, lane 2 is a sample of the lentiviral shuttle vector pRRL-CMV-heavy chain doubly enzymatically digested with Age I and Sal I, and lane 3 is a sample of the lentiviral shuttle vector pRRL-CMV-light chain doubly enzymatically digested with Age I and Sal I. The results of enzymatic digestion show a vector band of 7500 bp, and target gene bands of 1400 bp (heavy chain) and 700 bp (light chain), proving the successful construction of the lentiviral expression plasmids for the light and heavy chain of the chimeric antibody.

Figure 6:
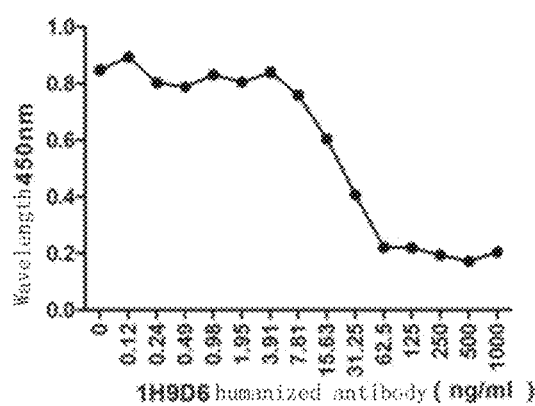
FIG. 6 is a diagram showing the results of testing the targeting of a c-MET humanized chimeric antibody in Example 6 of the present invention.

FIG. 6 shows the results of testing the targeting of a c-MET humanized chimeric antibody in Example 6 of the present invention, in which the abscissa represents the concentration of a c-MET humanized chimeric antibody in ng/ml, and the ordinate represents the absorbance at a wavelength of 450 nm. The results show that the c-MET humanized chimeric antibody can block the specific binding of HGF/MET, and with the increase of the concentration thereof added, the blocking effect thereof is increased. Under this system condition, the maximum blocking ratio of the c-MET humanized chimeric antibody against the specific binding of HGF/c-MET is 79.7%.

Figure 7:
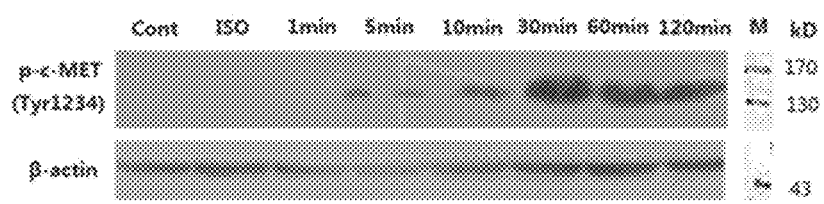
FIG. 7 is a diagram showing the result of detecting c-MET Tyr1234 phosphorylation in Bend.3 cells induced by a c-MET humanized chimeric antibody for a different period of time in Example 7 of the present invention.

FIG. 7 shows the detection result of c-MET Tyr1234 phosphorylation in Bend.3 cells induced by a c-MET humanized chimeric antibody for a different period of time in Example 7 of the present invention.

Figure 8:
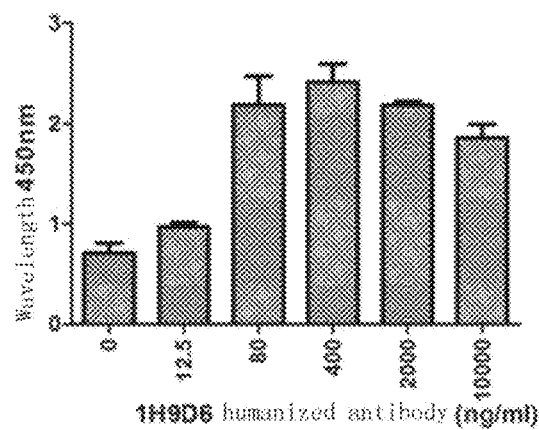
FIG. 8 is a diagram showing the detection results of in vitro binding activity of a c-MET humanized chimeric antibody in Example 8 of the present invention.

FIG. 8 shows the detection of in vitro binding activity of a c-MET humanized chimeric antibody in Example 8 of the present invention, in which the abscissa represents the loading concentration of the c-MET humanized chimeric antibody in ng/ml, and the ordinate represents the absorbance at a wavelength of 450 nm. The results show that the c-MET humanized chimeric antibody can specifically bind to the c-MET protein on the surface of HUVEC cells, and the signal is increased with an increasing concentration.

Figure 9:
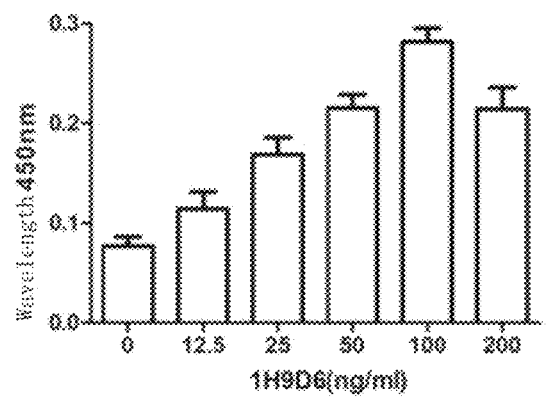
FIG. 9 is a diagram showing the effect of a c-MET monoclonal antibody on the proliferation of human umbilical vein endothelial cells (HUVECs) in Example 9 of the present invention.

FIG. 9 shows the effect of a c-MET monoclonal antibody on the proliferation of human umbilical vein endothelial cells (HUVECs) in Example 9 of the present invention, in which the abscissa represents the concentration of the c-MET monoclonal antibody in ng/ml, and the ordinate represents the absorbance at a wavelength of 450 nm. The results show that the c-MET monoclonal antibody can promote the proliferation of HUVEC cells, and the effect thereof is more significant with the increase of the concentration.

Figure 10:
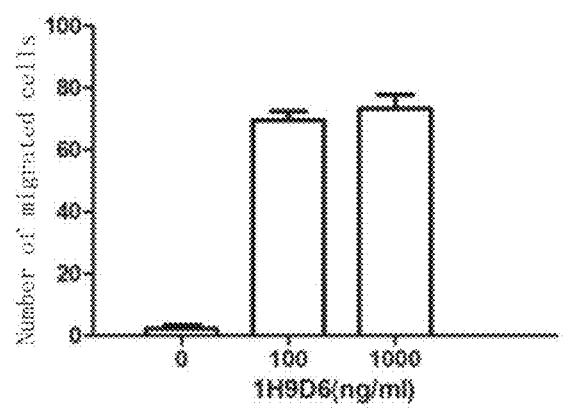
FIG. 10 is a diagram showing the effect of a c-MET monoclonal antibody on the migration of human umbilical vein endothelial cells (HUVECs) in Example 10 of the present invention.

FIG. 10 shows the effect of a c-MET monoclonal antibody on the migration of human umbilical vein endothelial cells (HUVECs) in Example 10 of the present invention, in which the abscissa represents the concentration of the c-MET monoclonal antibody in ng/ml, and the ordinate represents the number of cells on the lower surface of the transwell chamber. The results show that the c-MET monoclonal antibody can promote the migration of HUVEC cells, and the effect thereof is more significant with the increase of the concentration.

Figure 11:
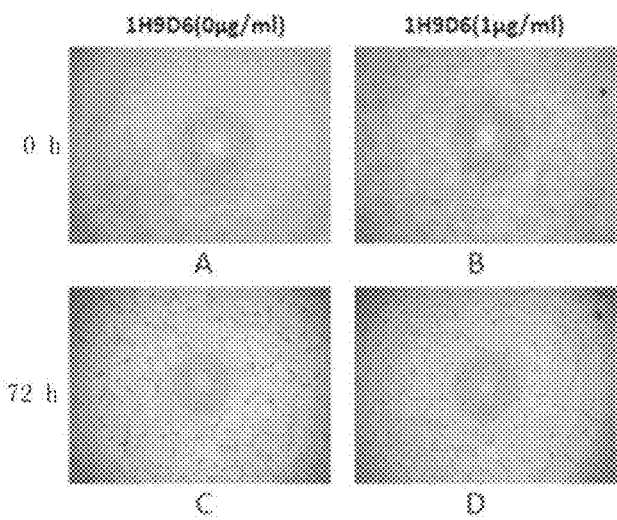
FIG. 11 is a diagram showing the effect of a c-MET monoclonal antibody on the microtubule formation of human umbilical vein endothelial cells (HUVECs) in Example 11 of the present invention.

FIG. 11 shows the effect of a c-MET monoclonal antibody on the microtubule formation of human umbilical vein endothelial cells (HUVECs) in Example 11 of the present invention, in which FIG. 11-A is a photograph of cells in a control group at 0 hour after matrigel spreading, FIG. 11-B is a photograph of cells in a group added with 1H9D6 with a concentration of 1 µg/ml at 0 hour after matrigel spreading, FIG. 11-C is a photograph of cells in a control group at 72 hours after matrigel spreading, and FIG. 11-D is a photograph of cells in a group added with 1H9D6 with a concentration of 1 µg/ml at 72 hours after matrigel spreading. Comparison between A and B shows that the initial state of cells is consistent. The comparison between C and D shows that 72 hours after treatment with 1H9D6 (1 µg/ml), the number of microtubules formed by HUVEC cells is increased significantly, proving that the c-MET monoclonal antibody can promote the microtubule formation of HUVEC cells.

Figure 12:
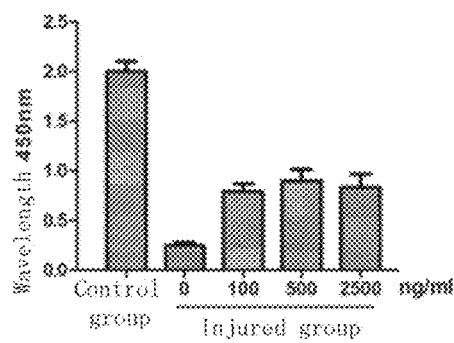
FIG. 12 is a diagram showing the protective effect of a c-MET humanized chimeric antibody on the activity of vascular endothelial cells (Bend.3) with oxygen-glucose deprivation in Example 13 of the present invention.

FIG. 12 shows the protective effect of a c-MET humanized chimeric antibody on the activity of vascular endothelial cells (Bend.3) with oxygen-glucose deprivation in Example 13 of the present invention, in which the abscissa provides sample information, wherein the control group is a sample without oxygen-glucose deprivation treatment, and the injured group is a sample with oxygen-glucose deprivation treatment, and the value in the protection group is the concentration of a c-MET humanized chimeric antibody in ng/ml; and the ordinate represents the absorbance at a wavelength of 450 nm. The results show that the c-MET humanized chimeric antibody has a protective effect on vascular endothelial cells (Bend.3) under oxygen-glucose deprivation, and the effect thereof is more significant with the increase of the concentration added.

Figure 13:
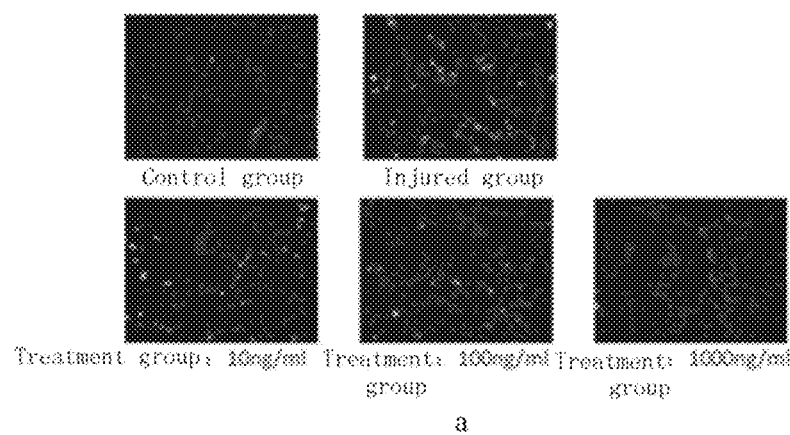
FIG. 13 is a diagram showing the protective effect of a humanized chimeric antibody on vascular endothelial cells (Bend.3) after oxygen-glucose deprivation against apoptosis in Example 14 of the present invention.
Figure 13:
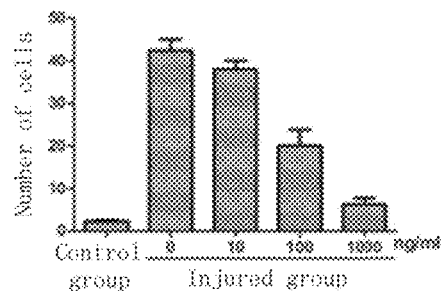

FIG. 13 shows the effect of a c-MET humanized chimeric antibody on apoptosis of vascular endothelial cells (Bend.3) after oxygen-glucose deprivation in Example 14 of the present invention. In FIG. 13-a, the control group is a sample without oxygen-glucose deprivation treatment, the injured group is a sample with oxygen-glucose deprivation treatment and the treatment group is a sample with oxygen-glucose deprivation and added with an anti-c-MET humanized antibody, wherein the value is the concentration of the anti-c-MET humanized antibody in ng/ml. FIG. 13-b shows the counts of apoptotic vascular endothelial cells (Bend.3) after oxygen-glucose deprivation treatment in the presence of the anti-c-MET humanized antibody. The results show that the number of apoptotic vascular endothelial cells (Bend.3) significantly is increased after oxygen-glucose deprivation treatment, and decreased with the addition of the anti-c-MET humanized antibody, proving that by the c-MET humanized chimeric antibody, vascular endothelial cells (Bend.3) subjected to oxygen-glucose deprivation are protected against apoptosis, and the protective effect thereof is more significant with the increase of the concentration of the anti-c-MET humanized antibody added.

Figure 14:
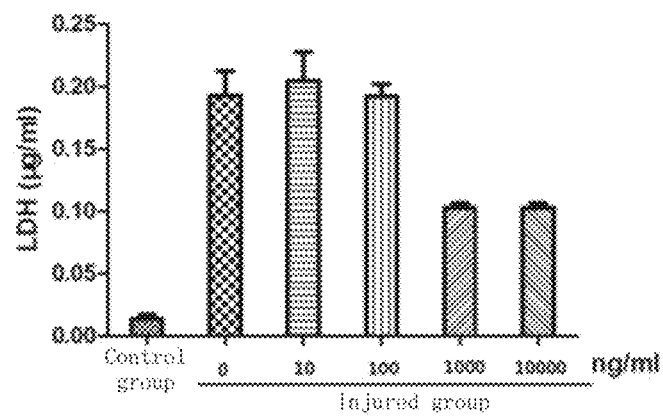
FIG. 14 is a diagram showing the concentration of released lactate dehydrogenase (LDH) after the death of vascular endothelial cells (Bend.3) with oxygen-glucose deprivation in the presence of a humanized chimeric antibody in Example 15 of the present invention.

FIG. 14 shows the effect of a c-MET humanized chimeric antibody on lactate dehydrogenase (LDH) indicative of vascular endothelial cell (Bend.3) death caused by oxygen-glucose deprivation in Example 15 of the present invention, in which the abscissa provides sample information, wherein the control group is a sample without oxygen-glucose deprivation treatment, the injured group is a sample with oxygen-glucose deprivation treatment, and the value in the treatment group is the concentration of the c-MET humanized chimeric antibody in ng/ml; and the ordinate represents the LDH concentration in μg/ml. The results show that, the LDH concentration is increased significantly after the oxygen-glucose deprivation treatment of vascular endothelial cells (Bend.3), and decreased with the addition of the anti-c-MET humanized antibody. It is shown that the c-MET humanized chimeric antibody has an effect to lower LDH concentration in oxygen-glucose deprived vascular endothelial cells (Bend.3), which is more significant with the increasing concentration of the anti-c-MET humanized antibody added.

Figure 15:
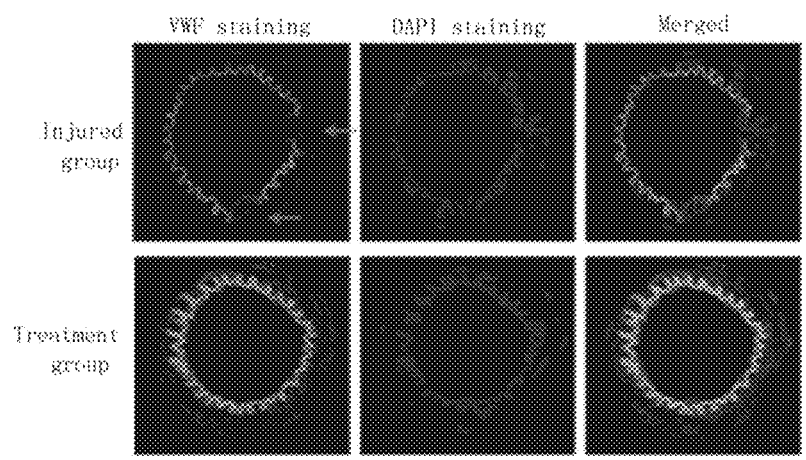
FIG. 15 is a diagram showing the protective effect of a c-MET monoclonal antibody on cerebral vascular endothelial cells in a SD rat model of photochemically induced focal cerebral ischemia in Example 17 of the present invention.

FIG. 15 shows the result of immunohistochemical staining of cerebrovascular endothelial cells showing the protective effect of a c-MET monoclonal antibody on cerebral vascular endothelial cells in a SD rat model of photochemically induced focal cerebral ischemia in Example 17 of the present invention, in which the injured group is injected with normal saline, the treatment group is injected with the c-MET monoclonal antibody at a dose of 1 mg/kg; VWF is a marker of vascular endothelial cells, DAPI is a marker of nuclear staining, and merged refers to an image generated by merging pictures stained for VWF and DAPI in the same field of view. The results show that the c-MET monoclonal antibody can significantly reduce the injury of cerebral vascular endothelial cells after photochemical injury, thereby maintaining a good vascular integrity and protecting against cerebral infarction in the SD rat model of photochemically induced focal cerebral ischemia.

Figure 16:
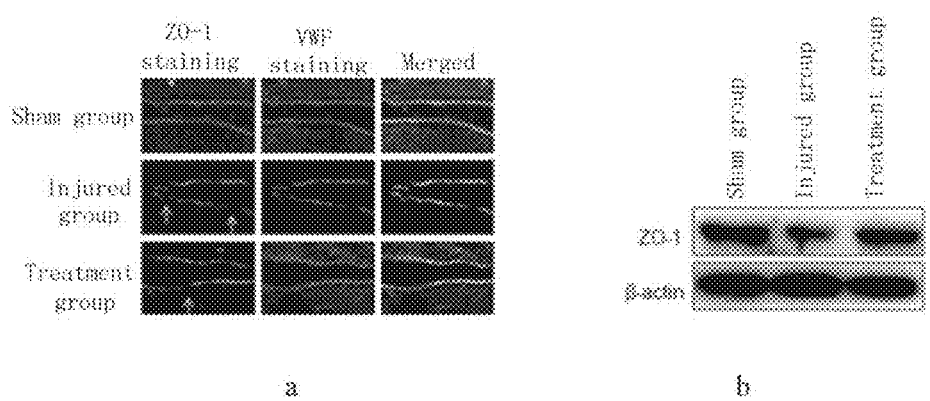
FIG. 16a-b shows the effect of a c-MET humanized chimeric antibody on the blood-brain barrier-related tight junction proteins in an in vivo model (a mouse MCAO model) in Example 17 of the present invention.

FIG. 16 shows a c-MET humanized chimeric antibody in an in vivo model (a mouse MCAO model) in Example 17 of the present invention. FIG. 16-a shows the effect of the c-MET antibody on the cerebral vascular endothelial cells and on the expression abundance of the tight junction protein ZO-1 in a mouse MCAO model for cerebral ischemia. In the sham group, a model is established by anesthetizing an animal with chloral hydrate and fixing on its back, then making a median incision in the neck to free the right common carotid artery, external carotid artery and internal carotid artery without injury. The injured group was injected with normal saline and the treatment group was injected with the purified 1H9D6 antibody at a dose of 1 mg/kg. VWF is a marker of vascular endothelial cells, ZO-1 is a tight junction protein, and merged refers to an image generated by merging pictures stained for VWF and ZO-1 in the same field of view. The results show that, as compared with the injured group, in the c-MET humanized chimeric antibody group, the ischemic penumbra of cerebral infarction exhibits a better microvascular integrity and a higher expression abundance of ZO-1, proving a less injured blood-brain barrier. FIG. 16-b shows the WB result showing the effect of a c-MET antibody on the expression abundance of the tight junction protein ZO-1 in an infarcted tissue in a mouse MCAO model for cerebral ischemia. In the sham group, a model is established by anesthetizing an animal with chloral hydrate and fixing on its back, then making a median incision in the neck to free the right common carotid artery, external carotid artery and internal carotid artery without injury. The injured group was injected with normal saline and the treatment group was injected with the purified 1H9D6 antibody at a dose of 1 mg/kg. β-actin is a housekeeping protein and used as a WB internal reference, and ZO-1 is a tight junction protein. The results show that the expression level of ZO-1 protein was significantly reduced in the injured group, and was the substantially same in the c-MET humanized chimeric antibody group and the sham group. It is shown that, the expression of ZO-1 protein in the mouse MCAO model is significantly reduced, which is in turn increased significantly by the c-MET humanized chimeric antibody, resulting in an level thereof close to that in the sham group.

Figure 17:
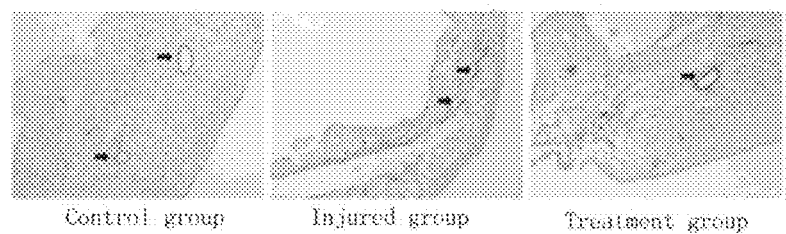
FIG. 17 is a diagram showing VWF staining of a tissue section from a heart infarction area in a mouse model of heart failure (a MI myocardial infarction model) with a c-MET humanized chimeric antibody in Example 17 of the present invention.

FIG. 17 shows the result of VWF staining of a tissue section from a heart infarction area in a mouse model of heart failure (a MI myocardial infarction model) with a c-MET humanized chimeric antibody in Example 17 of the present invention, in which the control group is a sham group, the mice in the injured group is injected with an equal amount of normal saline in the tail vein after MI myocardial infarction injury, and the mouse in the treatment group is injected with 3 mg/kg 1H9D6 humanized antibody in the tail vein after MI myocardial infarction injury. The results show that: the control group shows clear VWF staining and a clear and intact vascular structure; the injured group shows clear VWF staining and a severely injured vascular structure, indicating severe vascular injury caused by MI myocardial infarction; and the treatment group shows clear VWF staining and still maintains a relatively intact vascular structure, demonstrating that the anti-c-MET humanized antibody protects the cardiac microvessels against injury in the mouse model of heart failure (a MI myocardial infarction model).

Figure 18:
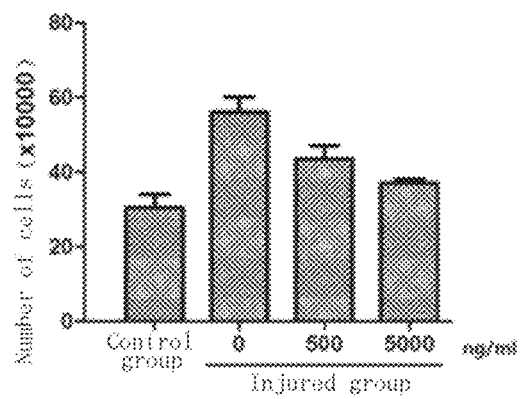
FIG. 18 is a diagram showing the effect of an anti-c-MET humanized chimeric antibody in an in vitro model of blood-brain barrier with oxygen-glucose deprivation in Example 18 of the present invention.

FIG. 18 shows the effect of an anti-c-MET humanized chimeric antibody in in vitro blood-brain barrier model with oxygen-glucose deprivation in Example 18 of the present invention, in which the abscissa provides sample information, wherein the control group is a sample without oxygen-glucose deprivation treatment, and the injured group is a sample with oxygen-glucose deprivation treatment, and the value in the injured group is the concentration of the anti-c-MET humanized chimeric antibody in ng/ml; and the ordinate represents the absorbance at a wavelength of 450 nm. The results show that after the oxygen-glucose deprivation treatment of vascular endothelial cells (Bend.3), the integrity of the cell layer is impaired, and the number of peripheral blood lymphocytes penetrating the cell layer in mice is significantly increased. The anti-c-MET humanized chimeric antibody has a protective effect in the in vitro blood-brain barrier model after oxygen-glucose deprivation, resulting in a reduced number of penetrated peripheral blood lymphocytes in mice, and the effect thereof is more significant with the increase of the concentration added.

Figure 19:
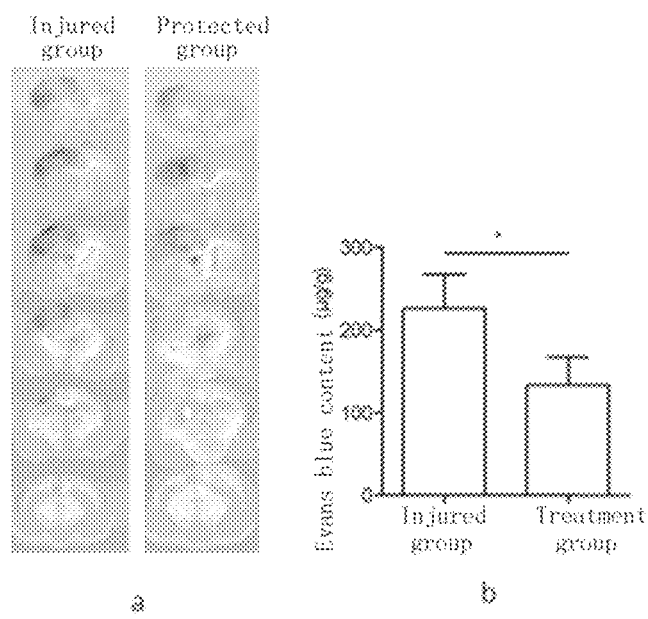
FIG. 19a-b shows the protective effect of a c-MET monoclonal antibody on blood-brain barrier permeability in a SD rat model of photochemically induced focal cerebral ischemia in Example 18 of the present invention.

FIG. 19 shows the protective effect of a c-MET antibody on blood-brain barrier permeability in a SD rat model of photochemically induced focal cerebral ischemia in Example 18 of the present invention. FIG. 19-a is a photograph of an animal brain tissue in which the injured group is injected with normal saline and the treatment group is injected with the c-MET monoclonal antibody at a dose of 1 mg/kg. FIG. 19-b shows the calculated Evans blue content, wherein the abscissa indicates the grouping, in which the injured group is injected with normal saline and the treatment group is injected with the c-MET monoclonal antibody at a dose of 1 mg/kg; and the ordinate represents the content of Evans blue in µg/g brain tissue. The results show that the c-MET monoclonal antibody can significantly reduce the content of Evans blue in the animal brain tissue after photochemical injury, and repair the blood-brain barrier permeability in the SD rat model of photochemically induced focal cerebral ischemia.

Figure 20:
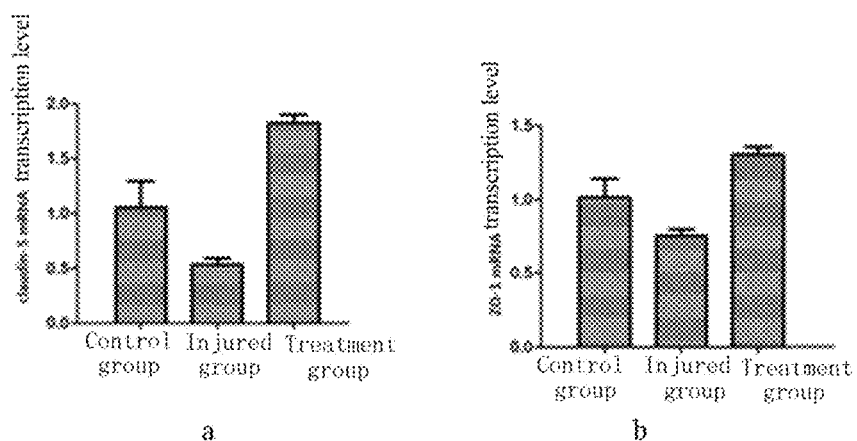
FIG. 20a-b shows the effect of a c-MET humanized chimeric antibody on the blood-brain barrier-related tight junction proteins in an in vitro model (a Bend.3 cell model) in Example 18 of the present invention.

FIG. 20 shows the effect of a c-MET humanized chimeric antibody on the blood-brain barrier-related tight junction proteins in an in vitro model (a Bend.3 cell model) in Example 18 of the present invention. FIGS. 20-a and 20-b show the results of fluorescent quantitative PCR of tight junction proteins claudin-5 and ZO-1 in the Bend.3 oxygen-glucose deprivation model, respectively, in which FIG. 20-a shows the result of the tight junction protein claudin-5, and FIG. 20-b shows the result of the tight junction protein ZO-1. The control group is a cell sample that has not been subjected to oxygen-glucose deprivation; the injured group is a cell sample that has been subjected to oxygen-glucose deprivation without the addition of the c-MET humanized chimeric antibody; and the treatment group is a cell sample that has been subjected to oxygen-glucose deprivation and added with the c-MET humanized chimeric antibody (with a concentration of 10000 ng/ml). The abscissa provides the sample information, and the ordinate represents the relative mRNA transcription level of each gene, with the mRNA transcription level of the target gene in the control group being 1.0. The results show that the mRNA transcription level of claudin-5 and ZO-1 proteins in vascular endothelial cells (Bend.3) is significantly reduced after oxygen-glucose deprivation, and with the addition of the c-MET humanized chimeric antibody, is increased significantly and exceeds that in the control group. It can be seen that, the c-MET humanized chimeric antibody significantly improves the mRNA transcription level of tight junction proteins in oxygen-glucose deprivated vascular endothelial cells.

Figure 21:
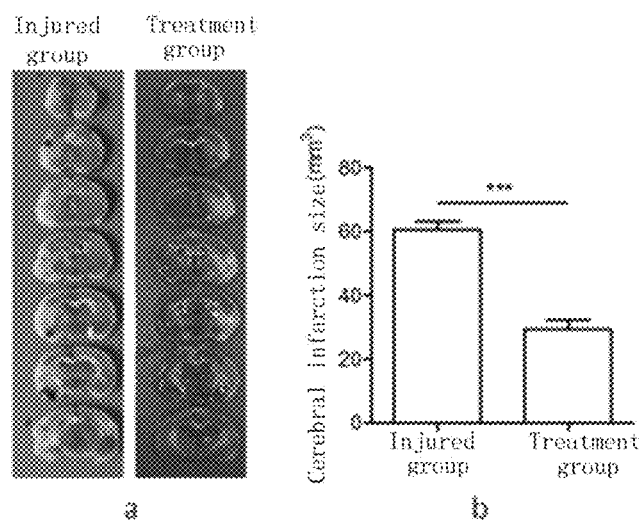
FIG. 21a-b shows the effect of a c-MET humanized chimeric antibody on the cerebral infarction size in a mouse MCAO model for cerebral ischemia in Example 19 of the present invention.

FIG. 21 shows the effect of a c-MET humanized chimeric antibody on cerebral infarction size in a mouse MCAO model for cerebral ischemia in Example 19 of the present invention. FIG. 21-a is a photograph of an animal brain tissue section, in which the injured group is injected with normal saline and the treatment group is injected with the c-MET humanized chimeric antibody at a dose of 1 mg/kg. FIG. 21-b shows the calculated cerebral infarction size. The abscissa indicates the grouping, in which the injured group is injected with normal saline and the treatment group is injected with the c-MET humanized chimeric antibody at a dose of 1 mg/kg; and the ordinate represents the cerebral infarction size in mm. The results show that the c-MET humanized chimeric antibody can significantly reduce the cerebral infarction size and protect against cerebral infarction in the mouse MCAO model for cerebral ischemia.

Figure 22:
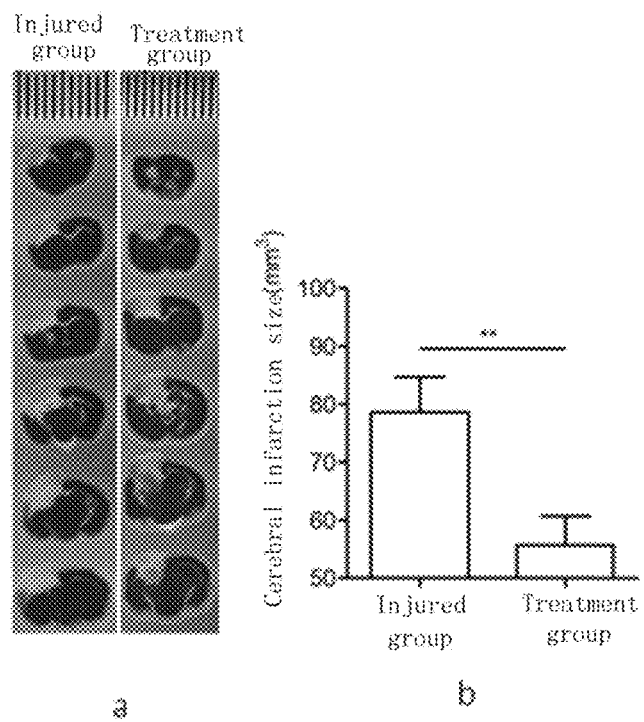
FIG. 22a-b shows the effect of a c-MET monoclonal antibody on the cerebral infarction volume in a SD rat model of photochemically induced focal cerebral ischemia in Example 19 of the present invention.

FIG. 22 shows the effect of a c-MET antibody on the cerebral infarction size in a SD rat model of photochemically induced focal cerebral ischemia in Example 19 of the present invention. FIG. 22-a is a photograph of an animal brain tissue section, in which the injured group is injected with normal saline and the treatment group is injected with a c-MET monoclonal antibody at a dose of 1 mg/kg. FIG. 22-b shows the calculated cerebral infarction size. The abscissa indicates the grouping, in which the injured group is injected with normal saline and the treatment group is injected with a c-MET monoclonal antibody at a dose of 1 mg/kg; and the ordinate represents the cerebral infarction size in $mm^3$. The results show that the c-MET monoclonal antibody can significantly reduce the cerebral infarction size in animals after photochemical injury and protect against cerebral infarction in the SD rat model of photochemically induced focal cerebral ischemia.

Figure 23:
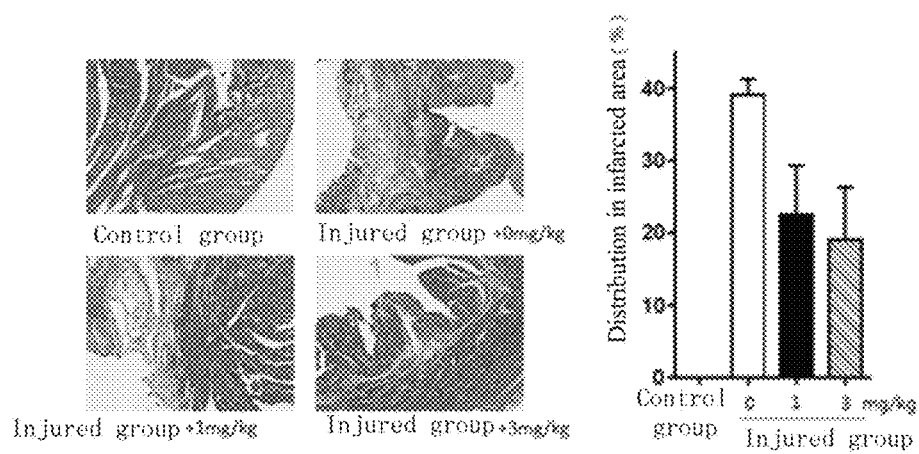
FIG. 23 is a diagram showing the Masson staining of a tissue section from the heart infarction area in a mouse model of heart failure (a MI myocardial infarction model) with a c-MET humanized chimeric antibody in Example 19 of the present invention.

FIG. 23 shows the Masson staining of a tissue section from the heart infarction area in a mouse model of heart failure (a MI myocardial infarction model) with a c-MET humanized chimeric antibody in Example 19 of the present invention. FIG. 23-a shows the results of Masson staining, in which collagen fibers are in green, muscle fibers are in red, and red blood cells are in orange-red; in which the control group is a sham group, the 0 mg/kg group in the injured groups is a separate injured group injected with an equal amount of normal saline in the tail vein after MI myocardial infarction injury, and the 1 mg/kg and 3 mg/kg groups in the injured groups are two treatment groups injected with c-MET humanized chimeric antibodies at 1 mg/kg or 3 mg/kg, respectively. FIG. 23-b shows the distribution ratio (collagen fibers/muscle fibers) in an infarcted area, in which the abscissa provides an mark for each group, in which the control group is a sham group, the 0 mg/kg group in the injured groups is a separate injured group injected with an equal amount of normal saline in the tail vein after MI myocardial infarction injury, and the 1 mg/kg and 3 mg/kg groups in the injured groups are two treatment groups injected with c-MET humanized chimeric antibodies at 1 mg/kg or 3 mg/kg, respectively; and the ordinate represents the ratio of collagen fiber/muscle fiber (%) in mouse heart. The results show that there is almost no positive staining of collagen fibers in the control group, while the staining of collagen fibers in the injured group is obvious, indicating severe myocardial fibrosis after MI myocardial infarction. In addition, the degree of fibrosis of myocardial tissue in the treatment groups is significantly reduced, which is more significant with the increase of the concentration of the c-MET humanized chimeric antibody, the reduction in fibrosis, demonstrating that the c-MET humanized chimeric antibody can inhibit cardiac fibrosis in the mouse model of heart failure (a MI myocardial infarction model).

Figure 24:
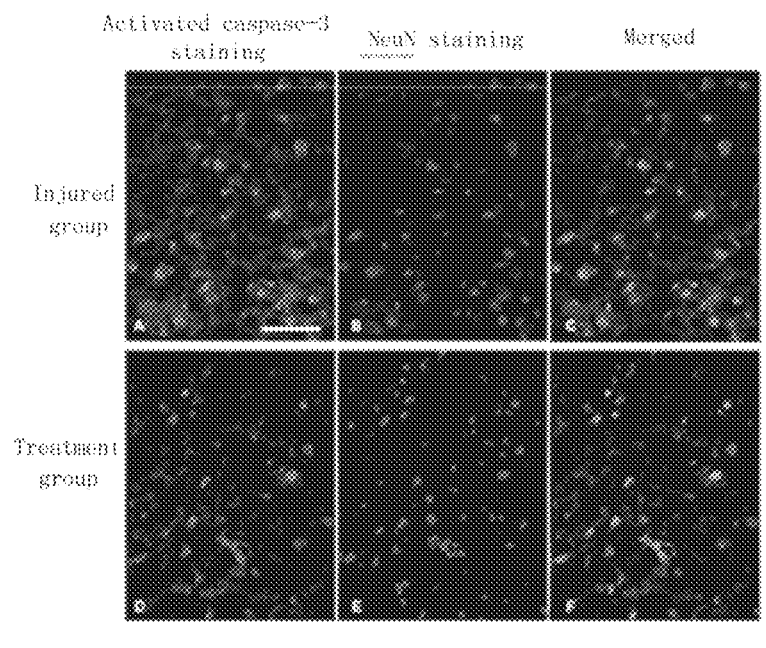
FIG. 24a-b shows the protective effect of a c-MET monoclonal antibody on neurons in a SD rat model of photochemically induced focal cerebral ischemia in Example 20 of the present invention.
Figure 24:
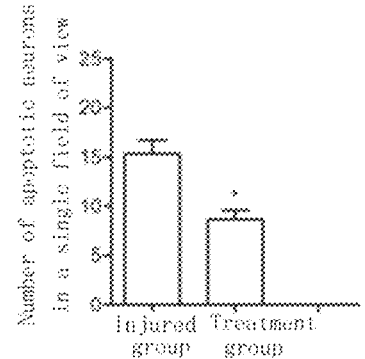

FIG. 24 shows the protective effect of a c-MET antibody on neurons in a SD rat model of photochemically induced focal cerebral ischemia in Example 20 of the present invention. FIG. 24-a shows the immunohistochemical staining of neurons in a cerebral infarction area, in which the injured group is injected with normal saline and the treatment group is injected with a c-MET monoclonal antibody at a dose of 1 mg/kg; activated caspase-3 is a marker of apoptosis, NeuN is a marker of blood neuronal cells, and merged refers to an image generated by merging pictures stained for activated caspase-3 and NeuN in the same field of view. FIG. 24-b is the count of apoptotic neurons in a single field of view. The abscissa indicates the grouping, in which the injured group is injected with normal saline and the treatment group is injected with a c-MET monoclonal antibody at a dose of 1 mg/kg; and the ordinate represents the number of apoptotic neurons. The results show that the c-MET monoclonal antibody can significantly reduce neuronal cell injury in the cerebral infarction area after photochemical injury, and thus significantly reduce the number of apoptotic neurons, therefore exhibiting a protective effect against cerebral infarction in the SD rat model of photochemically induced focal cerebral ischemia.

Figure 25:
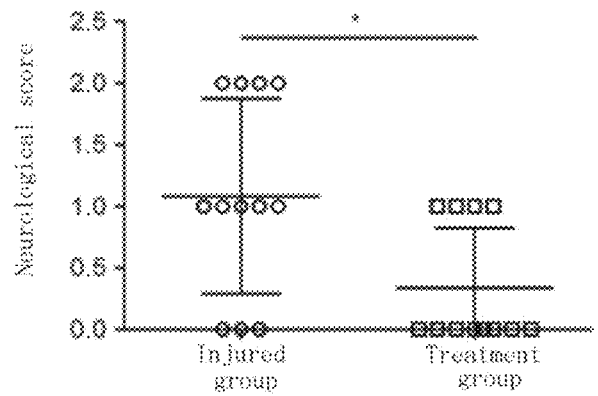
FIG. 25 is a diagram showing the protective effect of a c-MET monoclonal antibody on the neurological function in a SD rat model of photochemically induced focal cerebral ischemia in Example 20 of the present invention.

FIG. 25 shows the protective effect of a c-MET monoclonal antibody on the neurological function in a SD rat model of photochemically induced focal cerebral ischemia in Example 20 of the present invention. The abscissa indicates the grouping, in which the injured group is injected with normal saline and the treatment group is injected with the c-MET monoclonal antibody at a dose of 1 mg/kg; and the ordinate represents a neurological score, for which the scoring criteria are as follows:

0, no symptoms of neurological defects;
  1, slight neurological defects, unable to fully extend the left front paw;
  2, moderate focal neurological defects, turning to the left while walking;
  3, severe focal neurological defects, fall to the left; and
  4, inability to walk spontaneously, reduced level of consciousness.

The results show that the c-MET monoclonal antibody can significantly improve the neurological function in the animal after photochemical injury, and protect against cerebral infarction in the SD rat model of photochemically induced focal cerebral ischemia.

Figure 26:
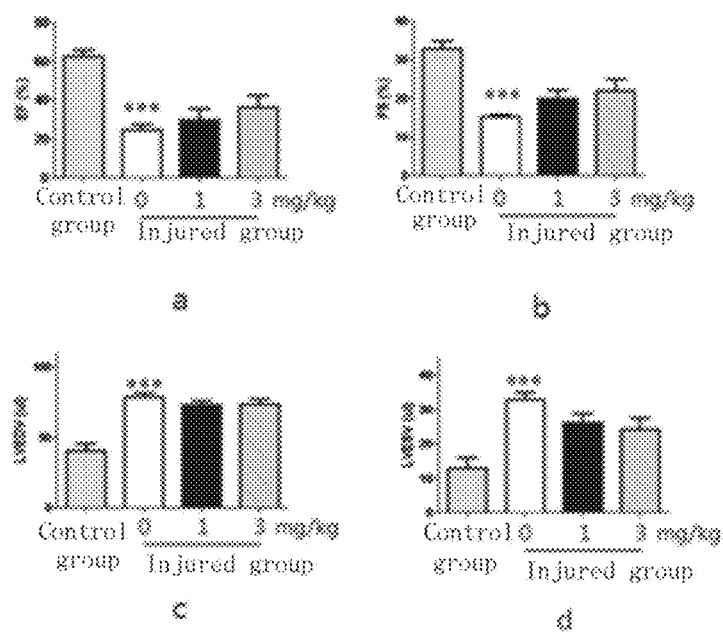
FIG. 26a-d shows the evaluation of cardiac function in a mouse heart failure model (a MI myocardial infarction model) in the presence of an anti-c-MET humanized chimeric antibody in Example 20 of the present invention.

FIG. 26 shows the evaluation of cardiac function in a mouse model of heart failure (a MI myocardial infarction model) in the presence of a c-MET humanized chimeric antibody in Example 20 of the present invention, as performed using echocardiography. FIG. 26-a shows the cardiac ejection fraction (EF), in which the abscissa provides an mark for each group, in which the control group is a sham group, the 0 mg/kg group in the injured groups is a separate injured group injected with an equal amount of normal saline in the tail vein after MI myocardial infarction injury, and the 1 mg/kg and 3 mg/kg groups in the injured groups are two treatment groups injected with c-MET humanized chimeric antibodies at 1 mg/kg or 3 mg/kg, respectively; and the ordinate represents the cardiac ejection fraction (EF) in the mouse, %. FIG. 26-b shows the left ventricular fractional shortening (FS), in which the abscissa indicates as in FIG. 26-a, and the ordinate represents the left ventricular fractional shortening (FS) in percentage (%). FIG. 26-c shows the left ventricular end-diastolic volume (EDV), in which the abscissa indicates as in FIG. 26-a, and the ordinate represents the left ventricular fractional shortening (FS) (μl). FIG. 26-d shows the left ventricular end-systolic volume (ESV), in which the abscissa indicates as in FIG. 26-a, and the ordinate represents the left ventricular end-systolic volume (ESV) (μl). The results show that: the EF in all the injured groups is less than 40%, indicating successful myocardial infarction modeling; after injection of 1 mg/kg/3d c-MET humanized chimeric antibody via tail vein, the EF has a tendency to recover; after injection of 3 mg/kg/3d c-MET humanized chimeric antibody via tail vein, the recovery of EF is more obvious. The FS, EDV and ESV all display a similar trend. Therefore, it is shown that the c-MET humanized chimeric antibody has a protective effect on cardiac function in mouse MI myocardial infarction model.

DETAILED DESCRIPTION

Unless otherwise defined, all technical and scientific terms used herein have the same meaning as understood by those of ordinary skill in the art. For definitions and terms in this field, professionals can in particular refer to Current Protocols in Molecular Biology (Ausubel). The abbreviation for amino acid residues is a standard 3-letter and/or 1-letter code used in the art to refer to one of the 20 commonly used L-amino acids. In particular, the meaning of the terms used herein can also be found in Chinese Patent Application No. 201110131029.X.

Although the numerical ranges and parameter approximations shown within the broad scope of the present invention, the numerical values shown in specific examples are recited as accurately as possible. However, an error is necessarily present in any numerical value, which is due to the standard deviation in their respective measurements. In addition, all ranges disclosed herein should be understood to encompass any and all subranges comprised therein. For example, a recited range of "from 1 to 10" should be considered to include any and all sub-ranges between the minimum value 1 and the maximum value 10 (including the end points); that is, all sub-ranges starting with the minimum value 1 or greater, for example, from 1 to 6.1, and all sub-ranges ending with the maximum value 10 or less, for example, from 5.5 to 10. In addition, any reference referred to as "incorporated herein" should be understood as being incorporated in its entirety.

It should also be noted that, as used in this specification, the singular form includes the plural form of the object to which it refers, unless clearly and explicitly limited to one object to which it refers. The term "or" may be used interchangeably with the term "and/or" unless the context clearly indicates otherwise.

As used herein, the term "soluble" protein refers to a protein that is soluble in an aqueous solution at a biologically relevant temperature, pH level, and osmotic pressure. In certain embodiments, the fusion protein of the invention is a soluble protein. As used herein, "soluble fusion protein" means that the fusion protein does not contain a transmembrane region and an intracellular region.

As used herein, the term "isolated" refers to a substance and/or entity that is (1) separated from at least some components originally associated therewith (in a natural environment and/or in a test setting) and/or (2) produced, prepared, and/or manufactured manually. An isolated substance and/or entity may be separated from at least about 10%, about 20%, about 30%, about 40%, about 50%, about 60%, about 70%, about 80%, about 90%, about 95%, about 98%, about 99%0, substantially 100%, or 100% of components originally associated therewith. In certain embodiments, the fusion protein of the invention is an isolated fusion protein.

The terms "portion" and "fragment" interchangeably refer to a part of a polypeptide, a nucleic acid, or other molecular constructs.

The term "subject" as used herein refers to a mammal, such as human, but may also refer to other animals, such as companion animals (such as dog, cat), domestic animals (such as cattle, sheep, pig, horse) or experimental animals (such as monkey, rat, mice, rabbit, guinea pig).

The terms "identity", "percent identity", "homology" or "identical" as used herein refer to sequence identity between two amino acid sequences or between two nucleic acid sequences. Percent identity can be determined by aligning two sequences, and refers to the number of identical residues (i.e., amino acids or nucleotides) at the positions shared by the compared sequences. Alignment and comparison of sequences can be performed using standard algorithms in the art (e.g., Smith and Waterman, 1981, Adv. Appl. Math. 2: 482; Needleman and Wunsch, 1970, J. MoI. Biol. 48: 443; Pearson and Lipman, 1988, Proc. Natl. Acad. Sci., USA, 85: 2444) or through computerized versions of these algorithms (Wisconsin Genetics Software Package Release 7.0, Genetics Computer Group, 575 Science Drive, Madison, Wis.), publically available as BLAST and FASTA. In addition, ENTREZ available at the National Institutes of Health (Bethesda Md.) can be used for sequence comparison. When using BLAST or Gapped BLAST programs, the default parameters of each program (e.g., BLASTN, available on the Internet site of the National Center for Biotechnology Information) can be used. In one embodiment, GCG with a gap weight of 1 can be used to determine the percent identity between two sequences so that each amino acid gap is given a weight as if it is a single amino acid mismatch between the two sequences. Alternatively, the ALIGN program (version 2.0) can be used, which is part of the GCG (Accelrys, San Diego, Calif.) sequence alignment software package.

Composition

The present invention further provides a pharmaceutical composition comprising an effective amount of the antibody or functional fragment thereof of the present invention, and a pharmaceutically acceptable carrier. Preferably, the antibody or functional fragment thereof is capable of binding to c-MET, wherein the antibody comprises a heavy chain and a light chain, and wherein:

the heavy chain comprises at least one heavy chain variable region sequence selected from SEQ ID NO: 9, SEQ ID NO: 10, SEQ ID NO: 11 and a mutant sequence thereof; and the light chain comprises at least one light chain variable region sequence selected from SEQ ID NO: 12, SEQ ID NO: 13, SEQ ID NO: 14, and a mutant sequence thereof.

Preferably, the mutant sequence as mentioned above means a sequence having at least 80% sequence identity, or at least 85% sequence identity, or at least 90% sequence identity, or at least 95% sequence identity, or at least 97%, 98% or 99% sequence identity compared with the original sequence.

As is well known in the art, the term "percent identity" describes the relationship between two or more polypeptide sequences or two or more polynucleotide sequences determined by comparing sequences. In the art, "identity" also refers to the degree of sequence relativeness between polypeptide or polynucleotide sequences as determined by the matches between these sequence strings, as the case may be. "Identity" or "similarity" can be easily calculated by known methods, including but not limited to those described in: Computational Molecular Biology (Edited by Lesk, A. M.) Oxford University Press, New York (1988); Biocomputing: Informatics and Genome Projects (Edited by Smith, D. W.) Academic Press, New York (1993); Computer Analysis of Sequence Data, Part I (Edited by Griffin, A. M. and Griffin, H. G.) Humana Press, New Jersey (1994); Sequence Analysis in Molecular Biology (Edited by von Heinje, G.) Academic Press (1987); and Sequence Analysis Primer (Edited by Gribskov, M. and Devereux, J.) Stockton Press, New York (1991). A preferred method of determining identity is designed to give the best matches between the measured sequences. Methods for determining identity or similarity have been written into publicly available computer programs. Sequence alignment and percent identity calculation can be performed using a sequence analysis software (e.g., the Megalign program in the LASERGENE Bioinformatics Calculation Suite (DNASTAR Inc., Madison, Wis.)).

In the pharmaceutical composition of the present invention, the antibody is comprised in a therapeutically effective amount. For example, the antibody or functional fragment thereof may account for 0.000001 wt % to 50 wt %, preferably 0.00001 wt % to 20 wt %, and more preferably 0.0001 wt % to 10 wt % of the pharmaceutical composition. Particularly preferably, the antibody or functional fragment thereof accounts for 0.001 wt % to 5 wt % of the pharmaceutical composition.

The composition of the present invention can be directly used to promote the repair and proliferation of vascular endothelial cells, especially in a disease caused by vascular injury. In addition, the composition can be used in combination with another therapeutic agent or adjuvant. Preferably, the pharmaceutical composition may further comprise one or more pharmaceutically active compounds for the treatment or prevention of an ischemic disease or ischemic injury of vascular endothelial cells.

Generally, the c-MET agonist of the present invention can be formulated in a non-toxic, inert and pharmaceutically acceptable aqueous carrier, wherein the pH is usually about 5-9, and preferably about 6-8.

As used herein, the term "containing" or "comprising" means that various ingredients can be used together in the mixture or composition of the present invention. Therefore, the terms "consisting mainly of" or "consisting of" are included in the term "containing" or "comprising". As used herein, the term "effective amount" or "effective dose" refers to an amount that can produce a function or activity in humans and/or animals and that is acceptable to humans and/or animals.

As used herein, "pharmaceutically acceptable" or "pharmacologically acceptable" ingredients are substances which are suitable for use in humans and/or mammals without excessive adverse side effects (such as toxicity, irritation, and allergies), that is, have a reasonable benefit/risk ratio. The term "a pharmaceutically acceptable carrier" refers to a carrier for administration with a therapeutic agent, including various excipients and diluents.

The composition of the present invention comprises a safe and effective amount of c-MET antibody and a pharmaceutically acceptable carrier. Such carriers include but are not limited to saline, buffer, glucose, water, glycerin, ethanol, or a combination thereof. Generally, the pharmaceutical preparation should be compatible with the mode of administration therefor. The pharmaceutical composition of the present invention can be prepared in the form of an injection, for example, by a conventional method using normal saline or an aqueous solution containing glucose and other adjuvant materials. The pharmaceutical composition is preferably manufactured under sterile conditions. The active ingredient is administered in a therapeutically effective amount. The pharmaceutical preparation of the present invention can also be formulated into a sustained-release preparation.

The effective amount of the c-MET antibody according to the present invention may vary depending on factors such as the mode of administration and the severity of the disease to be treated. A preferred effective amount can be determined by those of ordinary skill in the art based on various factors (e.g., through clinical trials), including but not limited to: the pharmacokinetic parameters of the c-MET antibody such as bioavailability, metabolism, half-life; the severity of the disease to be treated, the weight and immune status of the patient; the route of administration. Generally, when the c-MET antibody of the present invention is administered daily at a dose of about 0.00001 mg/kg-50 mg/kg animal body weight (preferably 0.0001 mg/kg-10 mg/kg animal body weight), satisfactory results would be achieved. For example, according to the urgency of the condition, several divided doses can be given daily, or the dose can be reduced proportionally.

In a preferred embodiment of the present invention, the antibody of the present invention is a humanized c-MET antibody, and achieves a better effect when administered at 0.1-500 mg/kg animal body weight per day. Preferably, the antibody is administrated at 0.5-200 mg/kg animal body weight per day; and more preferably 1-100 mg/kg animal body weight per day.

The administration of the c-MET antibody of the present invention is not particularly limited, and may be systemic or local. For example, the c-MET antibody of the present invention can be administered to animals by stereotactic injection in the brain, intraperitoneal injection, intravenous injection, oral administration, subcutaneous injection, intradermal injection, and the like, wherein intravenous injection is preferred.

After knowing the use of the c-MET antibody, various methods well known in the art can be used to administer the c-MET antibody or a coding gene thereof, or a pharmaceutical composition thereof to animals or human. Preferably, a recombinant protein of the c-MET antibody can be administered to a subject by injection or the like. Alternatively, gene therapy can be achieved by delivering an expression vector (such as a virus or a plasmid) carrying the gene of the c-MET antibody to a target organ and expressing the c-MET antibody protein in vivo.

As used herein, the terms "pharmaceutical composition", "combination drug", or "pharmaceutical combination" are used interchangeably, and means a combination of at least one drug and optionally a pharmaceutically acceptable carrier or adjuvant material combined together to achieve a particular purpose. In certain embodiments, the pharmaceutical composition comprises a combination that is separated in time and/or space as long as it can work together to achieve the object of the present invention. For example, the components contained in the pharmaceutical composition (for example, the antibody, nucleic acid molecule, nucleic acid molecule combination, and/or conjugate according to the present invention) may be administered to a subject as a whole or separately. When the ingredients contained in the pharmaceutical composition are separately administered to a subject, the ingredients can be administered to the subject simultaneously or sequentially. Preferably, the pharmaceutically acceptable carrier is water, buffered aqueous solution, isotonic salt solution such as PBS (phosphate buffered saline), glucose, mannitol, dextrose, lactose, starch, magnesium stearate, cellulose, magnesium carbonate, 0.3% glycerin, hyaluronic acid, ethanol or polyalkylene glycols such as polypropylene glycol, triglycerides. The type of the pharmaceutically acceptable carrier used depends, inter alia, on whether the composition according to the invention is formulated for oral, nasal, intradermal, subcutaneous, intramuscular or intravenous administration. The composition according to the invention may contain a wetting agent, an emulsifier or a buffer substance as an additive.

The pharmaceutical composition of the present invention can be delivered to a desired site using any method well known in the art. Examples of useful delivery devices include, but are not limited to, catheter (e.g., balloon catheter, infusion catheter, Stilettocatheter, needle, needleless syringe, stent, infusion sleeve, net, cardiacharness, Shunt, cardiac pacemaker, implantable defibrillator, suture, nail, perivascularwrap, flexible sheet or membrane substantially conforming to the contour of a wound site, tubing, graft, and pump. Specific examples of the method for delivering a HGF isoform include, but are not limited to, by a balloon catheter placed in a vein that flows into the coronary sinus (e.g., great cardiac vein, central cardiac vein, left ventricular posterior vein, anterior interventricular vein, or any other branch); by a catheter that leads into the lumen of one or more coronary arteries (such as the right coronary artery or the left coronary artery), in which the HGF isoform is coated on the balloon to be inflated at this site or injected from the catheter tip; delivery through a needle during open-heart surgery or heart transplantation (for example into the left atrium or right atrium, or the left ventricle or right ventricle); delivery to the pericardial cavity through the left atrium, right ventricle, or left ventricle via an internal entrance or to the pericardial area via an external entrance during open-heart surgery or micro-interventional surgery, or delivery to the pericardial area by injection, catheterization, laser-induced perfusion channel formation, cannula insertion, via an percutaneous entrance formed by using a particle gun or using a pump; delivery by antegrade perfusion in a catheter placed in a vessel that delivers blood to a tissue, or delivery by retrograde perfusion in a catheter placed in a vessel that receives blood from a tissue; or delivery by an endoluminal device or endovascular prosthesis (e.g. a stent, graft, stent-graft, vena cava filter) used to maintain vascular patency. In an embodiment, the device is biodegradable, thus avoiding the need to remove it after it is no longer needed. In some embodiments, two HGF isoforms are delivered using a stent. In yet another embodiment, the stent is selected from stainless steel stents that are not polymer-based, polymer-based stainless steel stents, cobalt-chromium stents that are not polymer-based and polymer-based cobalt-chromium stents.

The pharmaceutical composition according to the present invention may be administered by any suitable route, for example, oral, nasal, intradermal, subcutaneous, intramuscular, or intravenous administration.

The term "therapeutic agent" as used herein refers to any substance or entity capable of playing a therapeutic role (e.g., treating, preventing, relieving or inhibiting any disease and/or condition), including but not limited to a chemotherapeutic agent, radiotherapy agent, immunotherapeutic agent, thermally therapeutic agent.

As used herein, "CDR region" or "CDR" refers to the hypervariable region of the heavy and light chain of an immunoglobulin, as defined by Kabat et al. (Kabat et al., Sequences of proteins of immunological interest, 5th Ed., U.S. Department of Health and Human Services, NIH, 1991, and later). There are three heavy chain CDRs and three light chain CDRs. Depending on the circumstances, the term CDR or CDRs used herein is used to indicate one of these regions, or several or even all of these regions, which region contains most of the amino acid residues responsible for binding based on the affinity of an antibody for an antigen or its recognition epitope.

For the purpose of the present invention, "identical", "identity" or "similarity" between two nucleic acid or amino acid sequences refers to the percentage of the same nucleotide or amino acid residues between the two sequences to be compared obtained after the optimal alignment. The percentage is purely statistical and the differences between the two sequences are randomly distributed and cover their full length. Comparisons between two nucleic acid or amino acid sequences are usually performed by comparing these sequences after aligning them in an optimal manner, and can be performed over a segment or over a "comparison window". In addition to manual implementation, the optimal alignment used for comparing sequences can also be performed by the local homology algorithm of Smith and Waterman (1981) [Ad. App. Math. 2:482], by the local homology algorithm of Neddleman and Wunsch (1970) [J. Mol. Biol. 48:443], by the similarity search method of Pearson and Lipman (1988) [Proc. Natl. Acad. Sci. USA 85:2444), or by a computer software using these algorithms (GAP, BESTFIT, FASTA and TFASTA in the Wisconsin Genetics Software Package, Genetics Computer Group, 575 Science Dr., Madison, Wis., or by a comparison software BLAST N or BLAST P).

As used herein, "therapeutically effective amount" or "effective amount" refers to a dose sufficient to demonstrate a benefit when administered to a subject. The actual amount administered, as well as the frequency and time course of administration will depend on the condition and severity of the subject to be treated. General practitioners and other doctors are ultimately responsible for the treatment prescription (for example, decision on the dose) and usually make decisions based on the disease being treated, the condition of the individual patient, the delivery site, the mode of administration, and other factors known to the doctor.

The term "subject" as used herein refers to a mammal, such as human, but may also refer to other animals, such as wild animals (such as heron, stork, crane), domestic animals (such as duck, geese) or experiments animals (such as orangutan, monkey, rat, mice, rabbit, guinea pig, marmot, ground squirrel).

The term "antibody" refers to an intact antibody and any antigen-binding fragment ("antigen-binding portion") or single chain thereof. "Full-length antibody" refers to a protein comprising at least two heavy (H) chains and two light (L) chains interconnected by disulfide bonds. Each heavy chain contains a heavy chain variable region (abbreviated as VH) and a heavy chain constant region. The heavy chain constant region contains three domains (CH1, CH2 and CH3). Each light chain contains a light chain variable region (abbreviated as VL) and a light chain constant region. The light chain constant region contains one domain, CL. The VH and VL regions can be further subdivided into multiple regions with a high variability, known as complementarity-determining regions (CDR), interspersed with more conserved regions known as framework regions (FR). Each of VH and VL is composed of three CDRs and four FRs, arranged from the amino terminal to the carboxy terminal in the following order: FR1, CDR1, FR2, CDR2, FR3, CDR3, FR4. These variable regions of the heavy and light chains contain a binding domain that interacts with an antigen. The constant region of an antibody can mediate the binding of the immunoglobulin to a tissue or factor in a host, including various cells in the immune system (such as effector cells) and the first component in the classical complement system (Clq). Chimeric or humanized antibodies are also encompassed by the antibodies according to the invention.

The term "humanized antibody" refers to an antibody that contains a CDR region derived from a non-human antibody, and the other parts of the antibody molecule are derived from one (or several) human antibody. Moreover, in order to preserve the binding affinity, some residues in the backbone (called FR) segment can be modified (Jones et al., Nature, 321:522-525, 1986; Verhoeyen et al., Science, 239:1534-1536, 1988; Riechmann et al., Nature, 332:323-327, 1988). The humanized antibody or fragment thereof according to the present invention can be prepared by techniques known to those skilled in the art (for example, described in Singer et al., J. Immun. 150:2844-2857, 1992; Mountain et al., Biotechnol. Genet. Eng. Rev., 10:1-142, 1992; or Bebbington et al., Bio/Technology, 10:169-175, 1992).

The term "chimeric antibody" refers to an antibody in which the variable region sequence is derived from one species and the constant region sequence is derived from another species, for example, the variable region sequence is derived from a mouse antibody and the constant region sequence is derived from a human antibody. The chimeric antibody or fragment thereof according to the present invention can be prepared by using genetic recombination technology. For example, the chimeric antibody can be produced by cloning recombinant DNA comprising a promoter and a sequence encoding the variable region of the non-human and especially murine monoclonal antibody according to the present invention, and a sequence encoding the constant region of a human antibody. The chimeric antibody of the invention encoded by this recombinant gene will be, for example, a murine-human chimera, and the specificity of the antibody is determined by the variable region derived from murine DNA, and its isotype is determined by the constant region derived from human DNA. The method of preparing chimeric antibodies, for example, can be found in the Verhoeyn et al. (BioEssays, 8:74, 1988).

The term "monoclonal antibody" refers to a preparation of antibody molecules having a single molecular composition. The monoclonal antibody composition shows a single binding specificity and affinity for a specific epitope.

The term "derivative" refers to the (chemical) modification of an amino acid/amino acid chain at the N-terminus, C-terminus, backbone, peptide bond, and/or side chain residues thereof. The term is not intended to refer to any addition, substitution or deletion of amino acids in the amino acid chain. (Chemical) derivatives from such L-amino acids or L-amino acid enantiomers generally include any natural or non-naturally occurring derivatives of these amino acids, including but not limited to amino acids as defined above with a post-translational modification or synthetic modification, including acetylation (such as at the N-terminus of a (poly)peptide sequence, at a lysine residue), deacetylation, alkylation such as methylation, ethylation (preferably at a lysine or arginine residue in a (poly)peptide sequence), dealkylation such as demethylation, deethylation, amidation (preferably at the C-terminus of a (poly)peptide sequence), formylation, γ-carboxylation, glutamylation, glycosylation (preferably at a residue such as asparagine, lysine, hydroxylysine, serine or threonine in a (poly)peptide sequence), addition of heme or heme portion, hydroxylation, iodination, isoprenylation by which an isoprenoid portion such as farnesyl or geranylgeraniol is added, lipolation (connection of a lipoic acid functional group) such as isoprenylation, formation of a GPI anchor, including myristoylation, farnesylation, geranylgernaylation, oxidation, phosphorylation (e.g., at a serine, tyrosine, threonine or histidine moiety in a (poly)peptide sequence), sulfation (for example, sulfation of tyrosine), selenoylation, sulfation.

Administration

The fusion protein in the present invention can be administered alone, but is preferably administered as a pharmaceutical composition, which generally comprises a suitable pharmaceutical excipient, diluent or carrier selected according to the planned manner of administration. The fusion protein can be adapted to patients in need of treatment in any suitable manner. The precise dosage will depend on a number of factors, including the precise nature of the fusion protein.

Suitable modes of administration include but are not limited to oral, rectal, nasal, local (including buccal and sublingual), subcutaneous, vaginal, or parenteral (including subcutaneous, intramuscular, intravenous, intradermal, intrathecal and epidural) administration.

For intravenous injection or injection at a diseased site, the active ingredient will be in a form of a parenterally accepted aqueous solution that is non-pyrogenic and has a suitable pH, isotonicity, and stability.

Those skilled in the art can formulate a fusion protein with an appropriate solvent or formulating agent, such as an isotonic excipient such as sodium chloride injection, Ringer's injection, or lactated Ringer's injection. According to requirements, a preservative, stabilizer, buffer, antioxidant and/or other additives may be added. The pharmaceutical composition for oral administration may be in the form of such as tablets, capsules, powder, or oral liquid. Tablets may comprise a solid carrier, such as gelatin or an adjuvant. Liquid pharmaceutical compositions generally comprise a liquid carrier such as water, petroleum, animal or vegetable oil, mineral oil or synthetic oil. It may also comprise physiological saline solution, glucose or other sugar solutions or glycols, such as ethylene glycol, propylene glycol or polyethylene glycol.

Examples of the technologies and solutions mentioned above and some other technologies and solutions used according to the present invention can be found in Remington's Pharmaceutical Sciences, 16th edition, Oslo, A. (ed), 1980.

The c-MET antibody in the present invention may be naturally occurring, for example, may be isolated or purified from human or mammalian B lymphocytes or plasma cells. The c-MET antibody can also be prepared artificially. For example, animals can be immunized with a c-MET antigen, and monoclonal antibodies can be obtained through hybridoma technology.

The c-MET antigen may be a c-MET full-length protein, recombinant fragment or polypeptide, or a combination thereof. The animal may be a commonly used experimental animal. For example, a mouse anti-c-MET antibody is obtained by immunizing a mouse, and then is humanized by antibody engineering technology to prepare a monoclonal antibody suitable for medicine preparation. c-MET antibodies can also be obtained by immunizing or injecting a transgenic animal carrying human immunoglobulin genes, and directly obtaining fully human monoclonal antibodies by hybridoma technique. Alternatively, c-MET antibodies can also be obtained by screening B lymphocyte antibody libraries. The most commonly used technique is a phage antibody display technology to obtain fully human antibodies, and other display technologies are also possible, such as ribosome display, DNA antibody display, yeast antibody display. In the present invention, a recombinant c-MET protein is used to immunize an animal to obtain monoclonal antibodies. The amino acid sequence of the c-MET protein can be obtained according to the sequence set forth in GenBank accession number AAI0421.1.

In the present invention, an agonist c-MET antibody is obtained through hybridoma technology, combined with a protein and cell-level screening platform, and the amino acid sequence thereof is further obtained by gene cloning. For the specific method, see Example 2. The hybridoma cell line used to prepare the agonist c-MET antibody is deposited at the Chinese Type Culture Collection (Wuhan University, No. 299, Bayi Road, Wuchang District, Wuhan, Hubei) under the registration number CCTCC NO. C2017124 on Oct. 17, 2017. The amino acid sequences of the CDR regions of the c-MET antibody are set forth in SEQ ID NOs: 9-14.

It should be noted that if one or more amino acid residues are substituted, deleted or added in this sequence, the function of the antibody will still be maintained. The c-MET antibody or biologically active fragment thereof comprises a sequence with substitution of some conservative amino acids, which does not affect the activity or remains a part of the activity. Appropriate substitutions of amino acids or fragments are techniques well known in the art, and can be easily implemented with ensuring that the binding, activation, or inhibitory activity of the resulting molecules to the antigen would not be altered. With these techniques, those skilled in the art realize that, in general, changing a single amino acid in a non-essential region of an antibody does not substantially change the biological activity thereof. Therefore, variants of an antibody are not included in the present invention.

Any functional fragment (biologically active fragment) of the c-MET antibody can be used in the present invention. Here, a functional fragment of the c-MET antibody refers to a genetically engineered antibody fragment, which can still maintain all or part of the function of the full-length c-MET antibody. Usually, the functional fragment maintains at least 50% of the activity of the full-length c-MET antibody. More preferably, the functional fragment can maintain 60%, 70%, 80%, 90%, 95%, 99%, or 100% of the activity of the full-length c-MET antibody.

The present invention may also use modified or improved c-MET antibodies, for example, c-MET antibodies modified or improved to improve their half-life, effectiveness, metabolism, and/or protein efficacy.

The present invention can also employ chimeric or modified c-MET antibodies that comprise homologous fragments from other species. For example, humanized c-MET antibodies modified to reduce human heterogeneity can be used.

The modified or improved c-MET antibody may have little in common with the naturally occurring c-MET antibody, but still can promote the repair and proliferation of injured vascular endothelial cells without causing other adverse effects or toxicity. That is, any variant that does not affect the biological activity of the c-MET antibody can be used in the present invention.

In a preferred embodiment of the present invention, the c-MET antibody includes but is not limited to a humanized antibody, CDR-engineered chimeric antibody, FR-engineered chimeric antibody, Fc-engineered chimeric antibody.

According to the amino acid sequence of the c-MET antibody, the corresponding nucleotide coding sequence can be easily obtained.

In a preferred embodiment of the present invention, the c-MET antibody includes but is not limited to an expression vector or expression construct that can express (preferably overexpress) the c-MET antibody after being transferred into cells. Generally, the expression vector comprises a gene cassette containing a gene encoding the c-MET antibody and an expression control sequence operatively linked thereto. "Operatively linked" refers to a condition where certain parts of a linear DNA sequence can regulate or control the activity of other parts of the same linear DNA sequence. For example, if a promoter controls the transcription of a sequence, it is operatively linked to the coding sequence.

In the present invention, the c-MET antibody sequence can be comprised in a recombinant expression vector. Any plasmid or vector can be used in the present invention as long as it can be replicated and stable in the host. An important feature of an expression vector is that it usually contains an origin of replication, a promoter, a marker gene, and translation control elements.

Methods well known to those skilled in the art can be used to construct expression vectors containing the DNA sequence of the c-MET antibody and appropriate transcription/translation control signals. These methods include in vitro DNA recombination, DNA synthesis, in vivo recombination and so on. The DNA sequence can be operatively linked to an appropriate promoter in an expression vector to guide mRNA synthesis. The transformation vector further comprises a ribosome binding site for translation initiation and a transcription terminator.

In a preferred embodiment of the present invention, the c-MET antibody can be recombinantly expressed to achieve large-scale production. For the purpose of production, a gene encoding the c-MET antibody can be cloned into a suitable vector (such as a conventional prokaryotic or eukaryotic expression plasmid or a virus) by molecular biological methods, the vector is introduced into a cell expressing the c-MET antibody, and the cell is cultured to express the c-MET antibody to achieve the expression of the c-MET antibody. There are many types of cells, either eukaryotic or prokaryotic cells, for expression. In order to obtain antibodies with the best biological activity, it is preferable to use mammalian cells, and more preferably, CHO cells, for expression.

EXAMPLES

The present invention will be further described below in conjunction with specific examples.
Part 1: Screening and Producing a c-MET Agonistic Antibody In the present invention, initially a c-MET monoclonal antibody was obtained by hybridoma technology, and further humanized into a chimeric antibody. Then, ac-MET antibody which was capable of functioning as an agonist was screened based on the binding ability to the target and the activity to promote the phosphorylation of c-MET of the c-MET antibody.

Example 1. c-MET Antigen Cloning and Expression

As a ligand recognition site, the extracellular region of c-MET recognizes and binds to hepatocyte growth factor (HGF), and plays an important role in the subsequent series of biological regulation effects. Therefore, the extracellular region of c-MET was selected as an antigen. A c-MET extracellular region fragment (about 2800 bp) was amplified using the PCR primers based on the gene sequence of human c-MET in GenBank (accession number: NM_001127500.1): upstream primer P1 (5'-3'): TATACCGGTCGCCACCAT-GAAGGC CCCCGCTGTGCTTGCACCTG (SEQ ID NO: 1), and downstream primer P2 (5'-3'): CGCGTCGACCTA GTGATGGTGA TGATGGTGTG TGAAATTCTG ATCTGGTTG ACATA (SEQ ID NO: 2). The obtained DNA fragment was inserted into the lentiviral expression vector pRRL-CMV between two restriction sites, Age I and Sal I, and the insertion of the fragment was verified by agarose gel electrophoresis. The results are shown in FIG. 1a. In FIG. 1a, lane 1 is a DNA marker, and lane 2 is a sample of the lentiviral shuttle vector pRRL-CMV-ED digested with restriction enzymes Age I and Sal I. The results of enzymatic digestion show a vector band of 7500 bp and a target gene band of 2700 bp, proving the successful construction of the lentiviral expression vector pRRL-CMV-ED for the ED fragment of the extracellular region of human MET. The expression plasmid and a packaging plasmid were co-transfected into HEK293T cells, and the cell expression supernatant was purified through a nickel column, and subjected to polyacrylamide gel electrophoresis detection. The results are shown in FIG. 1b. In FIG. 1b, lane 1: an expression supernatant stock solution (1:5 dilution); lane 2: a column passing solution (1:5 dilution); lane 3: elution fractions with 20 mM Imidazole; lanes 4-5: elution fractions with 50 mM Imidazole; lanes 6-9: elution fractions with 200 mM Imidazole; M: a protein molecular weight standard. The 105 KDa band in lanes 5-9 was consistent with the expected target band, proving the successful expression and purification of the fusion protein with the extracellular region ED of MET.

The purified c-MET extracellular region protein was used for immunization or screening.

The DNA sequence expressed by the clone is a sequence encoding DNA of the extracellular region of human c-MET, represented by SEQ ID NO: 3; and its amino acid sequence is represented by SEQ ID NO: 4.

Example 2. Preparation of a c-MET Monoclonal Antibody

The recombinantly expressed c-MET extracellular region was diluted to 1 mg/ml with PBS (Hyclone, Cat No.: SH30256.01B), and emulsified with a Freund's adjuvant (a complete Freund's adjuvant for the primary immunization, and incomplete Freund's adjuvant for the booster immunization), then subcutaneously injected and inoculated into Balb/C mice (5 mice per group) at 100 μg antigen per mouse. The booster immunization was performed at two-week intervals. Starting from the first booster immunization, mouse serum was collected within 7 to 10 days after each booster immunization and the titer thereof was determined by ELISA.

Mice with a serum titer higher than 1:10000 after immunization were selected for cell fusion. Mouse B cells and myeloma cells (SP2/0-Ag14, Cell Bank of Chinese Academy of Sciences) were prepared aseptically and counted, respectively. The two types of cells were mixed at a ratio of SP2/0:B cells=1:5 and centrifuged (1000 r/min, 10 min). The supernatant was discarded and 1 ml of 50% polyethylene glycol (Roche, REF: 10783641001) was added to the precipitate, and then 20 ml of serum-free RPMI1640 (hyclone, Cat No.: SH30809.01) was added for termination of the reaction. After centrifugation for 10 min, the supernatant was discarded and the pellet was resuspended with RPMI1640 containing serum (BI, REF: 04-001-1ACS) and HAT (Gibco, REF: 21060-017). The suspension was plated with $10^5$ B cells/well, 200 μl per well. After adding $10^5$ mouse peritoneal macrophages per well, the plate was placed in a cell culture incubator at 37° C. After culturing for 7 days, the medium was changed to RPMI1640 containing HT (Gibco, REF: 11067-030) and serum (BI, REF: 04-001-1ACS), 200 μl per well. Then, after 7 to 10 days, positive clones were detected by ELISA. The result is shown in FIG. 2, in which the abscissa represents the loading volume of the c-MET antibody hybridoma supernatant in μl, and the ordinate represents the absorbance at a wavelength of 450 nm. The results show that the hybridoma clone supernatant can substantially specifically bind to c-MET protein, and as the volume of the supernatant added is increased, the ELISA binding signal is increased, showing a better dose-effect relationship.

Example 3. Binding Experiment of a c-MET Monoclonal Antibody to Target (ELISA)

In order to detect the ability of the c-MET antibody of the present invention to recognize and bind to the target c-MET, an enzyme-linked immunosorbent assay was used to test the affinity of the antibody (including hybridoma supernatant or recombinantly expressed monoclonal antibody) for an antigen in vitro.

Experimental procedure: the antigen (c-MET extracellular region, Example 1) was diluted to 2 µg/ml with a coating solution (CBS) (0.05M Carbonate-Bicarbonate, pH 9.6), and then the mixture was added to a 96-well microplate (Costar 9018, Cat No.: 03113024) at 100 µl/well and the plate was incubated at 4° C. overnight. The next day, the 96-well microplate coated with the antigen was returned to room temperature, and washed twice with a washing solution (PBS+0.05% Tween 20 (Sigma, Cat No.: P1379)). Subsequently, a blocking solution (PBS+1% BSA (sigma, Cat No.: V900933)) was added in 200 µl/well, and the plate was incubated at 37° C. for 2 hours, and washed three times with a washing solution. The test c-MET antibody was added into the 96-well microplate, and the plate was incubated at room temperature for 2 hours and then washed three times with a washing solution. A secondary antibody (Goat anti-Mouse IgG (H+L) (HRP) (Hangzhou Hua'an, Catalog No.: HA1006) diluted 5000 times with the blocking solution was added to the 96-well microplate at 100 µl/well, and the plate was incubated at room temperature for 1 hour and then washed three times with the washing solution. A color developing solution TMB (Beyotime Biotechnology, Catalog No.: P0209) was added into the 96-well microplate at 100 µl/well, followed by a stop solution (2M H2SO4) at 50 µl/well. A microplate reader (Bio-Rad, iMark) was used to read the plate at 450 nm.

The results are shown in FIG. 3, in which the abscissa represents the concentration of the c-MET antibody in ng/ml, and the ordinate represents the absorbance at a wavelength of 450 nm. The results show that: the c-MET antibody can specifically bind to the fusion protein with the extracellular region ED of MET, and as the added concentration thereof is increased, the signal is increased. Under this system condition, the minimum detection concentration of the c-MET monoclonal antibody is 0.06 ng/ml, proving that the c-MET antibody 1H9D6 has a strong binding ability to the fusion protein with the extracellular region ED of MET.

Example 4. Cloning of the c-MET Monoclonal Antibody Sequence

The single-cell c-MET antibody 1H9D6 with a good activity obtained in Example 3 was cloned for cDNA sequence, and then a monoclonal antibody was recombinantly expressed therefrom and tested for various activities. In the present invention, the genes of the heavy chain and light chain variable regions of the antibody were amplified by reverse transcription PCR, and connected into a vector for sequencing the light and heavy chain sequences of the obtained monoclonal antibody. Firstly, total cell RNA was extracted from the c-MET antibody hybridoma cell line secreting c-MET by the TRIzol method, and reverse transcribed into cDNA. Subsequently, using the synthesized cDNA as a template, the genes of the heavy and light chain variable regions VH and VL of the mouse monoclonal c-MET antibody were amplified by calling using a full set of murine-derived antibody heavy chain and light chain genes and degenerate primers. Heavy chain: upstream primer VH-F: SAR GTR MAG CTG MAG SAG TC (SEQ ID NO: 5), downstream primer: Mouse IgG R: AATTTTCTTGTC-CACCTTGGTGCTGCT (SEQ ID NO: 6). Light chain: upstream primer Mouse Vκ-F: GAY ATT GTD MTS ACM CAR WCT (SEQ ID NO: 7), downstream primer Mouse Cκ-R: GGATACAGTTGGTGCAGCATCAGCCC (SEQ ID NO: 8). The electrophoresis results are shown in FIG. 4, in which lane 1 is a DNA marker, lane 2 is the PCR product of the VH gene, and lane 3 is the PCR product of the VL gene. The electrophoresis results show the specific bands of the PCR products of mouse-derived VH and VL genes at about 351 and 336 bp, respectively, proving the successful calling of the mouse-derived VH and VL genes.

The PCR product finally amplified was cloned into a PCR-Blunt vector and sequenced. By IMGT database alignment, the mouse-derived CDR sequences in the present invention are set forth as in Table 1:

TABLE 1

| Mouse-derived CDR sequences | |
|---|---|
| Antibody | 1H9D6 |
| Heavy chain CDR1 | GYSFTSYW (SEQ ID NO: 9) |
| Heavy chain CDR2 | IDPSDSES (SEQ ID NO: 10) |
| Heavy chain CDR3 | ARSGYHGTSYWYFDV (SEQ ID NO: 11) |
| Light chain CDR1 | KSLLHSDGITY (SEQ ID NO: 12) |
| Light chain CDR2 | QMS (SEQ ID NO: 13) |
| Light chain CDR3 | AQNLELPPT (SEQ ID NO: 14) |

Example 5. Construction of a c-MET Humanized Chimeric Antibody

The genes of the heavy chain and light chain variable regions of the c-MET antibody were connected to human IgG1 heavy chain constant region gene Cγ1 and human light chain constant region gene Cκ respectively by overlap extension PCR to construct a c-MET chimeric antibody. The results of 1.5% agarose gel showed that the PCR products of mouse VH and VL genes showed specific bands at about 351 and 336 bp, respectively, and the PCR products of human Cγ1 and Cκ genes showed specific bands at about 1000 and 350 bp, respectively, which are consistent with theoretical value. The SOE-PCR product was doubly enzymatically digested with Age I and Sal I, and connected into the lentiviral expression vector pRRL-CMV. The electrophoresis results are shown in FIG. 5, in which lane 1 is a DNA marker, lane 2 is a sample of the lentiviral shuttle vector pRRL-CMV-heavy light doubly enzymatically digested with Age I and Sal I, and lane 3 is a sample of the lentiviral shuttle vector pRRL-CMV-light chain doubly enzymatically digested with Age I and Sal I. The results of enzymatic digestion show a vector band of 7500 bp, and target gene bands of 1400 bp (heavy chain) and 700 bp (light chain), proving the successful construction of the lentiviral expression plasmid for the light and heavy chain of the c-MET humanized chimeric antibody.

Example 6. Detection of the Targeting of c-MET Humanized Chimeric Antibody

In order to test whether the humanized chimeric antibody of the present invention targets or is specific to the target c-MET, HGF, a natural ligand for c-MET, was used for competitive binding experiments.

Experimental procedure: the antigen (c-MET extracellular region, Example 1) was diluted to 2 µg/ml with a coating solution (CBS) (0.05M Carbonate-Bicarbonate, pH 9.6), and then the mixture was added to a 96-well microplate (Costar 9018, Cat No.: 03113024) at 100 µl/well and the plate was incubated at 4° C. overnight. The next day, the 96-well microplate coated with the antigen was returned to room temperature, and washed twice with a washing solution (PBS+0.05% Tween 20 (Sigma, Cat No.: P1379)). Subsequently, a blocking solution (PBS+1% BSA (sigma, Cat No.: V900933)) was added at 200 µl/well, and the plate was incubated at 37° C. for 2 hours, and washed three times with the washing solution. The test c-MET humanized chimeric antibody was added into the 96-well microplate, and the plate was incubated at room temperature for 1.5 hours and then washed three times with the washing solution. HGF (RD, 294-HG) diluted with the blocking solution to a final concentration of 15 ng/ml was added at 100 µl/well, and the plate was incubated at 37° C. for 2 hours and then washed three times with the washing solution. A HGF antibody (RD, AF276) diluted 2000-fold with the blocking solution was added into the 96-well microplate at 100 µl/well, and the plate was incubated at room temperature for 1 hour, and then washed three times with the washing solution. Streptavidin-HRP enzyme-labeled secondary antibody (CST, #3999) diluted 2000-fold with the blocking solution was added to the 96-well microplate at 100 µl/well, and the plate was incubated at room temperature for 0.5 hour, and then washed with the washing solution three times. A color developing solution TMB (Beyotime Biotechnology, Catalog No.: P0209) was added into the 96-well microplate 100 µl/well, followed by a stop solution (2M H2SO4) at 50 µl/well. A microplate reader (Bio-Rad, iMark) was used to read the plate at 450 nm.

The competitive binding of HGF against the c-MET humanized chimeric antibody is shown in FIG. 6, in which the abscissa represents the concentration of the c-MET humanized chimeric antibody in ng/ml, and the ordinate represents the absorbance at a wavelength of 450 nm. The results show that the c-MET humanized chimeric antibody can block the specific binding of HGF/MET, and the blocking effect thereof is increased with the increase of the concentration added. Under this system condition, the maximum blocking ratio of the c-MET humanized chimeric antibody against HGF/c-MET specific binding is 79.7%. It can be seen that, HGF can effectively inhibit the binding of the c-MET chimeric antibody to the antigen, indicating that the chimeric c-MET antibody targets the target c-MET.

Example 7. Verification of Dimerization and Phosphorylation of the Target by the c-MET Humanized Chimeric Antibody In order to detect the ability of the c-MET antibody, especially the humanized chimeric antibody of the present invention, to activate the target c-MET, Western blot was used to examine the effect of the antibody on autophosphorylation of the target tyrosine kinase region after dimerization.

Experimental procedure: Bend.3 cells were incubated in an FBS-free medium for 24 hours, and then 20 µg/ml c-MET humanized chimeric antibody was added thereto, and then incubated at 37° C. for 1 min, 5 min, 10 min, 30 min, 60 min or 120 min, respectively. Cells were disrupted with a SDS lysis solution, and Western Blot was used to detect Tyr1234 phosphorylated MET in the lysate.

As shown in FIG. 7, the c-MET humanized chimeric antibody can activate the phosphorylation of c-MET. The phosphorylation activation effect began to appear at 5 min, reached the maximum at 30 min, and continued without decreasing until 120 min, indicating that the c-MET humanized chimeric antibody is an agonist antibody.

Part 2: Screening for c-MET Antibodies Able to Promote the Reconstruction and Repair of the Vascular Endothelial System The injury of vascular endothelial cells is an important part in the pathological process of many diseases and screening of substances capable of enhancing their biological activity can provide drug precursors that promote the formation of new blood vessels and preserve the potential of injured blood vessels under vascular injury conditions. Studies show that c-MET has a high expression level in vascular endothelial cells, and has proved to be an effective target in diseases caused by vascular endothelial cell injury. Therefore, the present inventor uses human umbilical vein endothelial cells (HUVECs) as a model to screen c-MET antibodies and evaluate their potential therapeutic capabilities.

Example 8. Detection of the Binding of c-MET Humanized Chimeric Antibody to Target Cells In order to detect whether the antibody of the present invention binds to target cells, cell ELISA was used to detect the binding of the antibody to the surface of HUVEC, a cell highly expressing c-MET.

Experimental procedure: HUVEC cells in the logarithmic growth phase were dissociated and counted, and plated at a density of 20,000 cells/well in a 96-well cell culture plate previously coated with polyornithine (PRON). The next day, the plate was washed once with PBS, and fixed with 4% paraformaldehyde at room temperature for 30 min. After washing with PBS, the plate was blocked at room temperature for 60 min (blocking solution: 1% FBS/PBS (v/v)). Then, 8 concentrations (serial 5-fold dilution starting from 20 µg/ml) of c-MET humanized chimeric antibody were added to the corresponding wells to a final volume of 100 µl, and incubated at room temperature for 1 hour. The plate was washed with PBS for three times. 100 µl of a 5000-fold diluted secondary antibody (Goat anti-Mouse IgG (H+L) (HRP) (Hangzhou Hua'an, Catalog No. HA1006) was added to each well, and the plate was incubated at room temperature for 1 hour and then washed three times with PBS. A color developing solution TMB (KPL Catalog No. 53-00-01) was added into the 96-well microplate at 100 µl/well, followed by a stop solution (2M H2SO4) at 50 µl/well. A microplate reader (Bio-Rad, iMark) was used to read the plate at 450 nm.

The binding of c-MET humanized chimeric antibody to c-MET antigen on the surface of HUVEC is shown in FIG. 8, in which the abscissa represents the loading concentration of the c-MET humanized chimeric antibody in ng/ml, and the ordinate represents the absorbance at a wavelength of 450 nm. The results show that the c-MET humanized chimeric antibody can specifically bind to the c-MET protein on the surface of HUVEC cells, and with an increasing concentration added thereof, the signal is increased. It can be seen that, the humanized antibody can significantly bind to HUVEC. The above results indicate that the c-MET antibody has the ability to bind to antigenic targets on the surface of living cells.

Example 9. Effect of c-MET Monoclonal Antibody on the Proliferation of Human Umbilical Vein Endothelial Cells (HUVECs)

In order to test the function of the c-MET monoclonal antibody of the present invention, a human umbilical vein endothelial cell (HUVEC) was used as a model to evaluate the effect of c-MET monoclonal antibody to promote the proliferation of endothelial cells.

Experimental principle: the binding of c-MET antibody to c-MET can promote the dimerization and tyrosine phosphorylation of c-MET molecule, and further activate the downstream signaling pathway of c-MET, thereby promoting the proliferation of vascular endothelial cells.

Experimental procedure: $1\times10^5$ cells/mL human umbilical vein endothelial cells (HUVECs) were added at 50 µl/well to a 96-well cell culture plate (costar, #3799) in a medium of a HUVEC basal culture solution (Allcells, Cat No.: H004B)+1% fetal bovine serum (FBS) (BI, REF: 04-001-1ACS). After culturing the cells for 24 h, the test c-MET antibody was added at 50 µl/well and cultured in an incubator (Thermo, 3111) at 37° C. for 3 days. According to the instructions, a cell proliferation detection kit (CCK8) (DOJINDO, CK04) was used to detect cell proliferation. A microplate reader (Bio-Rad, iMark) was used to read the plate at 450 nm and the cells were counted.

The results of cell counting are shown in FIG. 9, in which the abscissa represents the concentration of c-MET monoclonal antibody in ng/ml, and the ordinate represents the absorbance at a wavelength of 450 nm. The results show that the c-MET monoclonal antibody can promote the proliferation of HUVEC cells, and the effect thereof is more significant with the increase of the concentration added. It can be seen that, HUVECs are proliferated more significantly under the action of the c-MET antibody. The above results indicate that the c-MET monoclonal antibody can promote vascular endothelial cell proliferation and has a potential to protect blood vessels.

Example 10. Effect of c-MET Monoclonal Antibody on Migration of Human Umbilical Vein Endothelial Cells (HUVECs)

In order to test the function of the c-MET antibody of the present invention to promote angiogenesis, a human umbilical vein endothelial cell (HUVEC) was used as a model to evaluate the effect of the c-MET antibody to promote endothelial cell migration.

Experimental principle: the binding of the c-MET antibody to c-MET can promote the dimerization and tyrosine phosphorylation of c-MET molecule, and further activate the downstream signaling pathway of c-MET, thereby promoting the migration of vascular endothelial cells.

Experimental procedure: $2\times10^5$ cells/mL human umbilical vein endothelial cells (HUVECs) were added at 500 µl/well to the upper chamber of the transwell chamber (BD, 353097), and 750 µl of a medium containing different concentrations of the test antibody was added to the lower chamber, in which the medium is a HUVEC basal culture solution (Allcells, Cat No.: H004B)+1% fetal bovine serum (FBS) (BI, REF: 04-001-1ACS). After cultured for 16 h, the cells were stained with crystal violet, and the cells in the lower chamber were counted under a microscope.

The results of cell counting are shown in FIG. 10, in which the abscissa represents the concentration of the c-MET monoclonal antibody in ng/ml, and the ordinate represents the number of cells on the lower surface of the transwell chamber. The results show that the c-MET monoclonal antibody can promote the migration of HUVEC cells, and the effect thereof is more significant with the increase of the concentration added. It can be seen that, HUVEC migrates more significantly under the action of c-MET antibody. The above results indicate that the c-MET monoclonal antibody can promote vascular endothelial cells to migrate to form vascular endothelial tissue, and has a potential to protect blood vessels.

Example 11. Effect of c-MET Monoclonal Antibody on Microtubule Formation of Human Umbilical Vein Endothelial Cells (HUVECs)

In order to test the function of the c-MET antibody of the present invention to promote angiogenesis, a human umbilical vein endothelial cell (HUVEC) was used as a model to evaluate the effect of the c-MET antibody to promote the formation of microtubules by endothelial cells.

Experimental principle: the binding of the c-MET antibody to c-MET can promote the dimerization and tyrosine phosphorylation of c-MET molecule, and further activate the downstream signaling pathway of c-MET, thereby promoting the differentiation of vascular endothelial cells and the formation of microtubules. This process is important in the reconstruction and repair of injured blood vessels.

Experimental procedure: $2\times10^5$ cells/mL human umbilical vein endothelial cells (HUVECs) were added at 100 µl/well to a 96-well cell culture plate (costar, #3799) precoated with poly-D-lysine (sigma, P7280) in a medium of a HUVEC complete culture solution (Allcells, Cat No.: H004). After 24 hours of cell culture, 50 µl/well matrigel (BD, 354234) was added. After incubation at 37° C. for 30 min, the test c-MET antibody was added at 200 µl/well, and the medium was a HUVEC basal culture solution (Allcells, Cat No.: H004B). The plate was incubated in an incubator (Thermo, 3111) 37° C. for 3 days. The microtubule formation was observed at 24 h, 48 h and 72 h, and the microtubule-forming activity of HUVEC cells by the test antibody was evaluated according to the number of microtubules.

The results of microtubule formation are shown in FIG. 11, in which FIG. 11-A is a photograph of cells in a control group at 0 hour after matrigel spreading, FIG. 11-B is a photograph of cells in a group added with c-MET monoclonal antibody with a concentration of 1 µg/ml at 0 hour after matrigel spreading, FIG. 11-C is a photograph of cells in a control group at 72 hours after matrigel spreading, and FIG. 11-D is a photograph of cells in a group added with c-MET monoclonal antibody with a concentration of 1 µg/ml at 72 hours after matrigel spreading. Comparison between A and B shows that the initial states of cells are consistent. The comparison between C and D shows that 72 hours after adding the c-MET monoclonal antibody (1 µg/ml), the number of microtubules formed by HUVEC cells is increased significantly, proving that the c-MET monoclonal antibody can promote the microtubule formation of HUVEC cells.

It can be seen that, the number of microtubules formed by HUVEC under the action of the c-MET antibody is more significant. The above results indicate that the c-MET monoclonal antibody can induce vascular endothelial cells to differentiate into microtubules, and has a potential to protect or promote the formation of, new blood vessels under conditions of vascular injury.

Part 3: Protection of Endothelial Cells by c-MET Antibody Against Injury and Apoptosis Oxidation of blood-brain endothelial cells is a main pathological factor for injury, in which ischemia-reperfusion of brain microvascular endothelial cells will cause changes in the expression of tight junction proteins on the surface thereof, thereby directly leading to increased permeability of the blood-brain barrier and exacerbating the harmfulness of cerebral ischemia. In the present invention, by studying the protection of vascular endothelial cells by a c-MET agonist against injury, apoptosis and injury of cerebral vascular endothelial cells caused by ischemia-reperfusion (I-R) were used as a model to evaluate the protection by the c-MET antibody in injured endothelial cells.

Example 12. Establishment of an Oxygen-Glucose Deprivation Model of Vascular Endothelial Cells (I-R)

The medium for vascular endothelial cells (Bend.3) was a DMEM basal culture solution (hyclone, SH30243.01)+ 10% fetal bovine serum (FBS) (BI, REF: 04-001-1ACS). After 24 hours of cell culture, the medium was changed to a DMEM basal culture solution with different concentrations of c-MET humanized chimeric antibody, and cells were cultured in an incubator (Thermo, 3111) at 37° C. for 16 h. Afterwards, an anaerobic bag (Mitsubishi Chemical, Cl) was used in an anaerobic tank (Mitsubishi Chemical, C31) to create a low-oxygen environment for anaerobic and glucose-free injury for 6 hours, in which the medium was a DMEM glucose-free culture solution (Gibco, 11966-025) with different concentrations of c-MET humanized chimeric antibody added. Then, the medium was changed to a DMEM basal culture solution with different concentrations of c-MET humanized chimeric antibody added, and cells were cultured in the incubator (Thermo, 3111) at 37° C. for 1.5 h.

Example 13. Detection of the Preservation of the Activity of Injured Endothelial Cells by c-MET Humanized Chimeric Antibody A Bend.3 glucose-oxygen deprivation model was established as described in Example 12. $8 \times 10^4$ cells/mL cells were added to a cell culture plate (costar, #3799) at 100 μl/well, and after treatment in groups using a 96-well plate, a cell proliferation detection kit (CCK8) (DOJINDO, CK04) was used according to the instructions to detect cell viability. A microplate reader (Bio-Rad, iMark) was used to read the plate at 450 nm.

The protective effect of c-MET humanized chimeric antibody on oxygen-glucose deprived vascular endothelial cells (Bend.3): the cell counting is shown in FIG. 12, in which the abscissa provides sample information, wherein the control group is a sample without oxygen-glucose deprivation treatment, and the injured group is a sample with oxygen-glucose deprivation treatment, and the value in the protection group is the concentration of c-MET humanized chimeric antibody in ng/ml; and the ordinate represents the absorbance at a wavelength of 450 nm. The results show that the c-MET humanized chimeric antibody displays a protective effect on vascular endothelial cells (Bend.3) under oxygen-glucose deprivation, and the effect thereof is more significant with the increase of the concentration added. It can be seen that, the c-MET humanized chimeric antibody has a protective effect on the oxygen-glucose deprived vascular endothelial cells.

Example 14. Detection of the Protection of Endothelial Cells by c-MET Humanized Chimeric Antibody Against Apoptosis A Bend.3 glucose-oxygen deprivation model was established as described in Example 12.2 ml of $1 \times 10^5$ cells/mL vascular endothelial cells (Bend.3) was added to a 35 mm cell culture dish with a coverslip for cells growing on the coverslip. After treatment in groups, vascular endothelial cells (Bend.3) on the coverslip were detected using the TUNEL apoptosis kit (Vazyme Biotech Co., Ltd., Nanjing, A112-01). The apoptosis of vascular endothelial cells (Bend.3) after oxygen-glucose deprivation treatment in the presence of the test antibody was evaluated according to the number of apoptotic cells.

Control group: cell samples without oxygen-glucose deprivation treatment;

Injured group: cell samples subjected to oxygen-glucose deprivation treatment; and Protection group: the value therein is the concentration of anti-c-MET humanized antibody in ng/ml.

The photograph of apoptotic cells are shown in FIG. 13-*a*, and the statistical results of the number of apoptotic cells are shown in FIG. 13-*b*. The results show that, the number of apoptotic vascular endothelial cells (Bend.3) significantly is increased after oxygen-glucose deprivation treatment, and decreased with the addition of the anti-c-MET humanized antibodies, proving that by the anti-c-MET humanized chimeric antibody, vascular endothelial cells (Bend.3) deprivated of oxygen-glucose are protected against apoptosis, and such an effect is more significant with the increase of the concentration of the anti-c-MET humanized antibody added.

Example 15. Effect of c-MET Humanized Chimeric Antibody on LDH Indicative of Death of the Endothelial Cells $8 \times 10^4$ cells/mL vascular endothelial cells (Bend.3) were added to a 96-well cell culture plate at 0.1 ml/well, and a Bend.3 glucose-oxygen deprivation model was established as described in Example 12. The supernatant of vascular endothelial cells (Bend.3) was tested by a LDH detection kit (NanJing JianCheng Bioengineering Institute, A020-2).

Control group: cell samples without oxygen-glucose deprivation treatment;

Injured group: cell samples subjected to oxygen-glucose deprivation treatment; and Protection group: The value therein is the concentration of the anti-c-MET humanized antibody in ng/ml.

The LDH concentration in the cell supernatant are shown in FIG. 14, and the results show that the LDH concentration in vascular endothelial cells (Bend.3) is increased significantly after the oxygen-glucose deprivation treatment, and decreased with the addition of the c-MET humanized chimeric antibody, proving that the c-MET humanized antibody has an effect to lower the LDH concentration in oxygen-glucose deprived vascular endothelial cells (Bend.3), which is more significant with the increase of the concentration of the c-MET humanized chimeric antibody added. The c-MET antibody on the surface can significantly reduce the mortality of endothelial cells under I/R environment.

Part 4: Effect of c-MET Antibody in Various Ischemic Diseases

To further verify the protective effect of the c-MET antibody on endothelial cells under pathological conditions and the role in related pathological processes, the present invention uses pathological models at cell level or as a whole to study the pharmaceutical effect of the c-MET antibody in cerebral ischemia (cerebral infarction) and myocardial ischemia (myocardial infarction), and describes the effect of the c-MET antibody on the changes in blood-brain barrier permeability caused by endothelial cell injury and secondary neuronal apoptosis and other pathological processes.

Example 16. Establishment of In Vitro Models for Ischemic Injury

1) Rat Model of Cold Light Source Photochemically Induced Focal Cerebral Infarction:

The basic principle for this model is that when the light-sensitive substance Rose Bengal is injected intravenously and reaches the microvessels through the circulatory system, it may undergo a photochemical reaction under the irradiation of light with a specific intensity to cause cerebral edema and focal cerebral infarction formed by platelet microthrombosis in the irradiated area of the brain. In the early stage, this model can lead to the opening of the blood-brain barrier, severe vasogenic brain edema, and microvascular thrombosis. Therefore, it can be used in the pathophysiological study of blood-brain barrier changes and microvascular injury after cerebral infarction, and can better simulate the pathological characteristics of the ischemic penumbra.

Experimental procedure: experimental animals were anesthetized with 10% chloral hydrate peritoneally at 3 mL/kg of body weight. After successful anesthesia, 5% Rose Bengal B was slowly injected through the tail vein at 1.5 mL/kg. The experimental animal was fixed on the rat stereotaxic instrument, cut off for the head hair, and disinfected with regular iodine. A median incision from 5 mm behind the midpoint of the binocular line to 5 mm in front of the midpoint of the binaural line was made, the skin and subcutaneous tissue were cut, the right periosteal was carefully peeled off, and bleeding was stopped by electrocoagulation. Part of the right skull and the bregma, i.e., the intersection between the sagittal suture and the coronal suture, were exposed. The skull region with a diameter of about 5 mm at 2.0 mm behind and 2.0 mm right the bregma, was removed while preserving the intact dura mater. The laser was about 1 cm away from the brain tissue, and covered with a light-proof paper with a hole with a diameter of about 4 mm, the light intensity was 10-12 KLUX, and the irradiation time was 5 min. After the operation, the head skin was sutured. During the irradiation, a thermometer was used to maintain body temperature and the vital signs of the rats were steady.

Sham group: the surgery was performed without irradiation.

Treatment group: c-MET antibody at 1 mg/kg was injected into the tail vein 20 minutes after irradiation.

Injured group: An equal amount of normal saline was injected through the tail vein.

2) Mouse MCAO Model for Cerebral Ischemia

Right middle cerebral artery occlusion (MCAO) model. The mice were weighed, anesthetized by intraperitoneal injection with a chloral hydrate solution of 10% by volume (300 mg/kg by mass), and fixed on their back. A median incision was made in the neck to free the right common carotid artery, external carotid artery and internal carotid artery. A 3-0 nylon thread was inserted through the external carotid artery incision and slowly advanced in the direction of the internal carotid artery entering into the cranial to block the middle cerebral artery, thereby resulting in focal cerebral ischemia. After 1.5 h, the nylon thread was pulled out for reperfusion for 24 h.

Sham group: the surgery was performed with no nylon thread inserted.

Treatment group: c-MET antibody of 1 mg/kg was injected into the tail vein after inserting a nylon thread.

Injured group: An equal amount of normal saline was injected into the tail vein.

3) Mouse Model for Myocardial Infarction

The mice were weighed, anesthetized by intraperitoneal injection with 1% pentobarbital sodium at 50 mg/kg, and fixed on their back. The tracheal tube was inserted under the gooseneck lamp, the skin was cut laterally between the second and third ribs, the oblique pectoralis major muscle was lifted and the medial longitudinal pectoralis minor muscle was pulled off to expose the chest cavity. The muscle between the second and third ribs was cut, and lifted up and a rib spreader was put therein (avoid touching the lungs) to expose the heart. The cardiac pericardium was removed with a sharp forcep, the heart was fixed with the left hand to expose the atrial appendage, and a needle holder was hold in the right hand to ligate the LAD at 3-5 mm from the lower edge of the atrial appendage with a 8-0 nylon thread, and then the color change and beating under the left ventricular ligation were observed. The ribs, muscles and skin were sutured with 5-0 sutures, the state of the mice was observed until spontaneous breathing could be restored, and then the breathing catheter was pulled out.

Sham group: Surgery was performed without ligation.

Treatment groups: a total of 2 groups, c-MET monoclonal antibodies at 1 mg/kg or 3 mg/kg were injected into the tail vein every 3 days for 30 days, a total of 10 injections.

Injured group: an equal amount of normal saline was injected into the tail vein as a control.

Example 17. The Protective Effect of c-MET Antibody on Endothelial Cells in an Ischemic Environment 1) In Vivo Protective Effect of c-MET Monoclonal Antibody on Cerebral Vascular Endothelial Cells in a SD Rat Model of Photochemically Induced Focal Cerebral Ischemia In order to determine whether the c-MET antibody of the present invention has a substantial protective effect on vascular endothelial cells after binding c-MET in vivo, immunohistochemical detection was performed on the focal ischemic sites of rats in the following groups to evaluate their vascular injury and repair.

Rat models of photochemically induced focal cerebral ischemia were established as described in Example 16, grouped, modeled, and administered. After anesthetizing, the animals were firstly heart-perfused with PBS at 37° C., and then perfused with 4% PFA (paraformaldehyde) at 4° C. for fixation, and finally the brain tissue was removed. The tissue block was embedded with OCT (a frozen section embedding agent) and then frozen sectioned to produce sections with a thickness of generally 12-16 μm. The frozen sections were blocked with 5% ordinary goat serum for 1 hour at room temperature, and then a primary antibody diluted with 5% ordinary goat serum was added overnight at 4° C. The next day, after washing with PBS for 3 times, the sections were incubated for 1 hour in the dark with the corresponding fluorescent secondary antibody. After washing with PBS for 3 times, the sections were fixed with a mounting medium and observed under a fluorescence microscope.

The staining results of brain microvascular endothelial cells are shown in FIG. 15, in which the injured group is injected with normal saline, the treatment group is injected with c-MET monoclonal antibody at a dose of 1 mg/kg; VWF is a marker of vascular endothelial cells, DAPI is a marker of nuclear staining, and merged refers to an image generated by merging pictures stained for VWF and DAPI in the same field of view.

The results show that the c-MET monoclonal antibody can significantly reduce the injury of cerebral vascular endothelial cells after photochemical injury to maintain a good vascular integrity, and protects against cerebral infarction in the SD rat model of photochemically induced focal cerebral ischemia.

It can be seen that, the degree of microvascular injury in the c-MET monoclonal antibody group is lower than that in the control group. The above results indicate that the c-MET monoclonal antibody can effectively protect the cerebral vascular endothelial system.

2) In Vivo Protective Effect of c-MET Humanized Chimeric Antibody on Cerebral Vascular Endothelial Cells in a Mouse MCAO Model for Cerebral Ischemia Mouse MCAO models were established as described in Example 16, grouped, modeled, and administered. After anesthetizing, the animals were firstly heart-perfused with PBS at 37° C., and then perfused with 4% PFA (paraformaldehyde) at 4° C. for fixation, and finally the brain tissue was removed. The tissue block was embedded with OCT (a frozen section embedding agent) and then frozen sectioned to produce sections with a thickness of generally 12-16 μm. The frozen sections were blocked with 5% ordinary goat serum for 1 hour at room temperature, and then a primary antibody diluted with 5% ordinary goat serum was added overnight at 4° C. The next day, after washing with PBS for 3 times, the sections were incubated for 1 hour in the dark with the corresponding fluorescent secondary antibody. After washing with PBS for 3 times, the sections were fixed with a mounting medium and observed under a fluorescence microscope.

The staining results of brain microvascular endothelial cells are shown in FIG. 16-*a*, in which the injured group is injected with normal saline and the treatment group is injected with the c-MET humanized chimeric antibody at a dose of 1 mg/kg; VWF (an endothelial cell marker) antibody and anti-ZO-1 (a tight junction protein) antibody; and merged refers to an image generated by merging pictures stained for VWF and ZO-1 in the same field of view. Western blot results of ZO-1 expression at the injured site are shown in FIG. 16-*b*.

The results show that the c-MET humanized chimeric antibody can significantly reduce the injury of cerebral vascular endothelial cells by light MCAO to maintain a good vascular integrity, and protects against MCAO model-induced endothelial system injury.

It can be seen that, the degree of microvascular injury in the c-MET humanized chimeric antibody group is lower than that in the control group. The above results indicate that the c-MET humanized chimeric antibody can effectively protect the cerebrovascular endothelial system.

3) The Protective Effect of c-MET Humanized Chimeric Antibody on Vascular Endothelial Cells in a Mouse Model for Heart Failure (MI Myocardial Infarction Model)

Mouse models for heart failure (MI myocardial infarction models) were established as described in Example 16 and grouped. The heart was quickly removed, fixed in 4% paraformaldehyde and embedded in paraffin. The heart 3 mm beneath the LAD ligation was cut to produce sections with a thickness of 3 mm and stained for VWF. Firstly, the sections were incubated with a VWF antibody at a 1:50 antibody dilution at room temperature for 120 minutes, and then washed 3 times with PBS. A HRP labeled anti-rabbit secondary antibody with a 1:500 antibody dilution was added, and the sections were incubated at room temperature for 30 minutes, and then washed 3 times with PBS. 1 drop of a freshly prepared DAB solution was added to each section and the sections were observed under the microscope for 5 minutes. The sections were differentiated with 0.1% HCl, washed with tap water, and blued. Then, the sections were dehydrated with graded ethanol and dried, hyalinized with xylene, sealed with neutral gum, and observed under a microscope after naturally drying.

Evaluation index: VWF is a marker of vascular endothelial cells. The distribution and status of vascular endothelial cells can be observed by immunohistochemistry of VWF to reflect the integrity of blood vessels. The effect of the c-MET humanized chimeric antibody on cardiac microvessels in mouse MI myocardial infarction model was evaluated.

Results: The VWF staining results of heart sections are shown in FIG. 17, in which the injured group is injected with an equal amount of normal saline, the treatment group is injected with c-MET humanized chimeric antibody at 3 mg/kg, and the control group is a sham group. The results show that: the control group shows clear VWF staining and a clear and intact vascular structure; the injured group shows clear VWF staining and severely injured vascular structure, indicating severe vascular injury caused by MI myocardial infarction; and the treatment group shows clear VWF staining and still maintains a relatively intact vascular structure, demonstrating that the anti-c-MET humanized antibodies protect against cardiac microvascular injury in the mouse model for heart failure (MI myocardial infarction model).

Example 18. The Protection Against Blood-Brain Barrier Penetration Caused by Ischemia by c-MET Antibody The increased permeability of the blood-brain barrier is an important pathological event after the injury of cerebrovascular endothelial cells, which can lead to secondary injury to brain tissue. Therefore, the present invention uses various models to verify the function of c-MET antibody to protect the blood-brain barrier.

1) Effect in Monolayer Bend.3 Blood-Brain Barrier Model after Glucose-Oxygen Deprivation $4 \times 10^4$ cells/mL vascular endothelial cells (Bend.3) were added at 500 μl/well to the upper chamber of the transwell chamber (BD, 353097), and 750 μl of medium was added to the lower chamber, in which the medium was a DMEM basal culture solution (hyclone, SH30243.01)+10% fetal bovine serum (FBS) (BI, REF: 04-001-1ACS). After cultured for 72 h, the medium was changed to a DMEM basal culture solution with different concentrations of c-Met humanized antibody added, and the cells were cultured in an incubator (Thermo, 3111) at 37° C. for 16 h. Afterwards, an anaerobic bag (Mitsubishi Chemical, Cl) was used in an anaerobic tank (Mitsubishi Chemical, C31) to create a low-oxygen environment for anaerobic and glucose-free injury for 6 hours, in which the medium was a DMEM glucose-free culture solution (Gibco, 11966-025), and in the treatment group, added with different concentrations of c-MET humanized chimeric antibody. Then, the medium was exchanged to a DMEM complete culture solution, which was a DMEM basal culture solution (hyclone, SH30243.01)+10% fetal bovine serum (FBS) (BI, REF: 04-001-1ACS). Different concentrations of c-MET humanized chimeric antibody were added. $1 \times 10^6$ mouse peripheral blood lymphocytes/well were added to the upper chamber, and cultured in an incubator (Thermo, 3111) at 37° C. for 24 hours. The mouse peripheral blood lymphocytes were stained with crystal violet on the bottom of the lower chamber, and the effect of the test antibody in the in vitro blood-brain barrier model of vascular endothelial cells (Bend.3) was evaluated according to the number of cells.

Control group: cell samples without oxygen-glucose deprivation treatment;

Injured group: Cell samples with oxygen-glucose deprivation treatment; and

Treatment group: Cell samples treated with different concentrations of c-MET humanized chimeric antibody under oxygen-glucose deprivation.

The counting results are shown in FIG. 18. The results show that after the oxygen-glucose deprivation treatment of vascular endothelial cells (Bend.3), the integrity of the cell layer is impaired, and the number of mouse peripheral blood lymphocytes penetrating the cell layer is significantly increased. The c-MET humanized chimeric antibody has a protective effect in the in vitro model of the blood-brain barrier after oxygen-glucose deprivation to reduce the number of penetrated mouse peripheral blood lymphocytes, which is more significant with the increase of the concentration added.

2) The Protective Effect of c-MET Monoclonal Antibody on the Permeability of Blood-Brain Barrier in a SD Rat Model of Photochemically Induced Focal Cerebral Ischemia In order to determine whether the c-MET antibody of the present invention has a substantial protective effect on the blood-brain barrier after binding c-MET in vivo, rat models of cold light source photochemically induced focal cerebral infarction were established as described in Example 16, grouped and tested for the permeability of the blood-brain barrier in rats in each group to evaluate the effect to maintain the blood-brain barrier.

Rat models of cold light source photochemically induced focal cerebral infarction were established as described in Example 16, grouped and administered. In order to observe the destruction of the blood-brain barrier based on Evans blue permeation, a 2% Evans blue physiological saline solution (4 mL/kg body weight) was injected through the tail vein 1 hour before the experimental animals were sacrificed at the corresponding time points. Thoracotomy and perfusion were performed. When the fluid flowing from the right atrial appendage was substantially clear, the rat was decapitated and the brain was removed. The cerebral hemisphere at the infarcted side was taken out, weighed and placed in 3 mL formamide solution, and incubated in a thermostatic water bath at 50° C. for 72 h. After centrifugation for 20 min (4000 r/min), the absorbance value of the supernatant was measured with a microplate reader (wavelength: 632 nm). The EB content was calculated according to the standard curve plotted for EB, and the results were expressed in µg/g brain tissue.

The permeation of EB into brain tissue is shown in FIG. 19, in which FIG. 19-a is a photograph of an animal brain tissue in which the injured group is injected with normal saline and the treatment group is injected with c-MET monoclonal antibody at a dose of 1 mg/kg; and FIG. 19-b shows the calculated Evans blue content. The abscissa indicates the grouping, in which the injured group is injected with normal saline and the treatment group is injected with c-MET monoclonal antibody at a dose of 1 mg/kg; and the ordinate represents the content of Evans blue in µg/g brain tissue.

The results show that the c-MET monoclonal antibody can significantly reduce the content of Evans blue in animal brain tissue after photochemical injury, and repair the blood-brain barrier with an increased permeability in the SD rat model of photochemically induced focal cerebral ischemia.

It can be seen that, the EB permeation in the c-MET monoclonal antibody group is significantly lower than that in the control group. The above results indicate that the c-MET monoclonal antibody can protect the blood-brain barrier.

3) Effect of c-MET Antibody on Tight Junction Protein Expression in Injured Endothelial Cells In Vitro Testing In vitro oxygen-glucose deprivation models were established as described in Example 12. The cell supernatant was discarded and the total RNAs were extracted from the cells. Fluorescent quantitative PCR analysis of the target gene was performed using primers specific for a different tight junction protein to obtain the mRNA transcription level of the target gene in samples in each group.

Control group: Cell samples without oxygen-glucose deprivation treatment.

Injured group: Cell samples subjected to oxygen-glucose deprivation treatment without the addition of c-MET humanized chimeric antibody.

Treatment group: Cell samples subjected to oxygen-glucose deprivation treatment and added with c-MET humanized chimeric antibody (concentration: 10000 ng/ml).

The results from fluorescent quantitative PCR are shown in FIGS. 20-a and 20-b, in which the abscissa provides the sample information, and the ordinate represents the relative mRNA transcription level of each gene, with the mRNA transcription level of the target gene in the control group being 1.0. FIG. 20-a shows the result of a tight junction protein ZO-1, and FIG. 20-b shows the result of a tight junction protein claudin-5. The results show that the mRNA transcription levels of claudin-5 and ZO-1 proteins in vascular endothelial cells (Bend.3) are significantly reduced after oxygen-glucose deprivation, and with the addition of the c-MET humanized chimeric antibody, is increased significantly and exceeds that in the control group. It can be seen that the c-MET humanized chimeric antibody significantly improves the mRNA transcription level of tight junction proteins in oxygen-glucose deprived vascular endothelial cells.

In Vivo Testing:

Mouse MCAO models for cerebral ischemia were established as described in Example 16. After treatment in groups, the mouse brain was taken out and cut into 1 mm thick sections. The brain sections were subjected to indirect immunofluorescence double staining, wherein an anti-VWF (an endothelial cell marker) antibody and anti-ZO-1 (a tight junction protein) antibody were added respectively to stain the microvessels in the ischemic penumbra from cerebral infarction, to evaluate the effect of the c-MET humanized chimeric antibody on the integrity of the blood-brain barrier and on the expression level of the tight junction protein ZO-1. The staining results are shown in FIG. 16-a. It can be seen that in the c-MET humanized chimeric antibody group, the microvascular integrity in the ischemic penumbra from the cerebral infarction is better and the expression abundance of ZO-1 is higher than that in the injured group, proving that the blood-brain barrier is less disrupted.

The brain of the mouse was taken out, and the region with cerebral infarction was ground with liquid nitrogen to prepare a sample, which was subjected to WB analysis of ZO-1 protein. WB results are shown in FIG. 16-b. The expression level of ZO-1 protein in the injured group was significantly reduced, while the expression level of ZO-1 protein in the c-MET humanized chimeric antibody group was substantially the same as that in the sham group, proving that the expression of ZO-1 protein is significantly decreased in the mouse MCAO model, which is significantly increased by the c-MET humanized chimeric antibody to a level close to that in the sham group.

Example 19. Effect of c-MET Antibody on Tissue Infarction in an Ischemic Model

In order to determine whether the c-MET antibody of the present invention has a substantial protective effect in the infarcted lesion site after binding c-MET in vivo, the cerebral infarction size in the focal ischemic site of mice in each group described in Example 12 was evaluated.

1) The Protective Effect of c-MET Humanized Chimeric Antibody Against Cerebral Infarction in Mouse MCAO Model for Cerebral Ischemia Mouse MCAO models for cerebral ischemia were established as described in Example 16 and grouped. After the treatment, the mouse brain was removed and cut into 2 mm thick sections, and then the brain sections were stained with 2% 2,3,5-triphenyltetrazolium chloride (TTC, in 0.9% normal saline) to determine the size of the infarcted area.

The cerebral infarction size is shown in FIG. 21, wherein FIG. 21-a is a photograph of an animal brain tissue section, in which the injured group is injected with normal saline and the treatment group is injected with c-MET humanized chimeric antibody at a dose of 1 mg/kg; and FIG. 21-b shows the calculated cerebral infarction size. The abscissa indicates the grouping, in which the injured group is injected with normal saline and the treatment group is injected with c-MET humanized chimeric antibody at a dose of 1 mg/kg; and the ordinate represents the cerebral infarction size in $mm^3$. The results show that the c-MET humanized chimeric antibody can significantly reduce the cerebral infarction size in the mouse MCAO model for cerebral ischemia and protect against cerebral infarction in the mouse MCAO model for cerebral ischemia.

It can be seen that, the cerebral infarction size in the c-MET humanized chimeric antibody group is significantly smaller than that in the control group. The above results indicate that the c-MET humanized chimeric antibody can reduce cerebral infarction tissue injury.

2) The Protective Effect of c-MET Monoclonal Antibody on the Brain Tissue in a SD Rat Model of Photochemically Induced Focal Cerebral Ischemia Photochemically induced cerebral infarction models were established as described in Example 16 and treated in groups. After operation, the rat brain was removed and cut into 2 mm thick sections, and then the brain sections were stained with 2% 2,3,5-triphenyltetrazolium chloride (TTC, in 0.9% normal saline) to determine the size of the infarcted area.

The cerebral infarction size is shown in FIG. 22, wherein FIG. 22-a is a photograph of an animal brain tissue section, in which the injured group is injected with normal saline and the treatment group is injected with c-MET monoclonal antibody at a dose of 1 mg/kg; and FIG. 22-b shows the calculated cerebral infarction size. The abscissa indicates the grouping, in which the injured group is injected with normal saline and the treatment group is injected with c-MET monoclonal antibody at a dose of 1 mg/kg; and the ordinate represents the cerebral infarction size in $mm^3$. The results show that the c-MET monoclonal antibody can significantly reduce the cerebral infarction size in animals after photochemical injury and protect against cerebral infarction in the SD rat model of photochemically induced focal cerebral ischemia.

The above results indicate that the c-MET monoclonal antibody can reduce cerebral infarction tissue injury.

3) The Protective Effect of c-MET Humanized Chimeric Antibody Against Myocardial Fibrosis in Mouse Model of Heart Failure (MI Myocardial Infarction Model)

Mouse models for heart failure (MI myocardial infarction models) were established as described in Example 16 and treated in groups. The heart was quickly removed, fixed in 4% paraformaldehyde and embedded in paraffin. The heart 3 mm beneath the LAD ligation was cut to produce sections with a thickness of 3 mm and the sections was subjected to Masson staining. Firstly, the sections were stained with a Masson compound staining solution for 5 minutes, and rinsed once with a 0.2% acetic acid aqueous solution. Then, the sections were treated with 5% phosphotungstic acid for 5 to 10 minutes, and rinsed twice with a 0.2% acetic acid aqueous solution. After that, the sections were stained with a bright green staining solution for 5 minutes, and rinsed twice with a 0.2% acetic acid aqueous solution. The sections were dehydrated with anhydrous ethanol, hyalinized with xylene, sealed with neutral gum, observed under a microscope and photographed.

Evaluation index: Masson staining is used to evaluate the level of fibrosis in a cardiac infarcted area, and observe the effect of c-MET antibody on myocardial fibrosis lesions in mouse MI myocardial infarction model.

Results: The results of Masson staining of heart sections are shown in FIG. 23, in which FIG. 23-a shows the results of Masson staining, and FIG. 23-b shows the result of the distribution ratio (collagen fibers/muscle fibers) in the infarcted area. The injured group is injected with an equal amount of normal saline; there are 2 treatment groups, which are injected with c-MET humanized chimeric antibody at 1 mg/kg or 3 mg/kg, respectively. The control group is a sham group. The results show that there is almost no positive staining of collagen fibers in the control group, while the staining of collagen fibers in the injured group is obvious, indicating severe myocardial fibrosis after MI myocardial infarction. In addition, the degree of fibrosis of myocardial tissue in the treatment groups is reduced significantly, and with the increase of the concentration of the c-MET humanized chimeric antibody, more significantly, demonstrating that the c-MET humanized chimeric antibody can inhibit myocardial fibrosis in the mouse model for heart failure (MI myocardial infarction model).

Example 20. Effect of c-MET Antibody on Physiological Function in an Ischemic Model 1) Protective Effect of c-MET Monoclonal Antibody on Neurons in a SD Rat Model of Photochemically Induced Focal Cerebral Ischemia In order to determine whether the c-MET antibody of the present invention has a substantial protective effect on neurons after binding to c-MET in vivo, immunohistochemical detection was performed on the neurons around the infarcted area in rats in each group described in Example 8 to evaluate the protective effect on neurons.

Rat models of photochemically induced focal cerebral ischemia were established as described in Example 16, grouped, and administered. After anesthetizing, the animals were firstly heart-perfused with PBS at 37° C., and then perfused with 4% PFA (paraformaldehyde) at 4° C. for fixation, and finally the brain tissue was removed. The tissue block was embedded with OCT (a frozen section embedding agent) and then frozen sectioned to produce sections with a thickness of generally 12-16 μm. The frozen sections were blocked with 5% ordinary goat serum for 1 hour at room temperature, and then a primary antibody diluted with 5% ordinary goat serum was added overnight at 4° C. The next day, after washing with PBS for 3 times, the sections were incubated for 1 hour in the dark with the corresponding fluorescent secondary antibody. After washing with PBS for 3 times, the sections were fixed with a mounting medium and observed under a fluorescence microscope.

The results from neuron staining are shown in FIG. 24, wherein FIG. 24-a shows the results from immunohistochemical staining of neurons in a cerebral infarcted area, in which the injured group is injected with normal saline and the treatment group is injected with c-MET monoclonal antibody at a dose of 1 mg/kg; activated caspase-3 is a marker of apoptosis, NeuN is a marker of blood neuronal cells, and merged refers to an image generated by merging pictures stained for activated caspase-3 and NeuN in the same field of view. FIG. 24-b is the statistical number of apoptotic neurons in a single field of view. The abscissa represents the grouping, in which the injured group is injected with normal saline and the treatment group is injected with c-MET monoclonal antibody at a dose of 1 mg/kg; and the ordinate represents the number of apoptotic neurons.

The results show that the c-MET monoclonal antibody can significantly reduce neuronal cell injury in the cerebral infarcted area after photochemical injury, and thus significantly reduce the number of apoptotic neurons, thereby providing protection against cerebral infarction in the SD rat model of photochemically induced focal cerebral ischemia. It can be seen that, the degree of neuronal injury in the c-MET monoclonal antibody group is lower than that in the control group. The above results indicate that the c-MET monoclonal antibody can protect neurons.

2) Effect of c-MET Monoclonal Antibody on Behavioral Symptoms in a SD Rat Model of Photochemically Induced Focal Cerebral Ischemia In order to determine the neurological protective effect of the c-MET antibody in rats with cerebral infarction, the neurological and behavioral evaluation of rats in each group described in Example 16 were performed. With reference to a 5-grade by 4-score method by Longa et al., neurological scores were performed after the mice were awake.

The scoring criteria are as follows:
  0, no symptoms of neurological defects;
  1, slight neurological defects, unable to fully extend the left front paw;
  2, moderate focal neurological defects, turning to the left while walking;
  3, severe focal neurological defects, fall to the left; and
  4, inability to walk spontaneously, reduced level of consciousness.

The behavioral evaluation results are shown in FIG. 25, in which the abscissa represents the grouping, in which the injured group is injected with normal saline and the treatment group is injected with c-MET monoclonal antibody at a dose of 1 mg/kg; and the ordinate represents the neurological score. The results show that the c-MET monoclonal antibody can significantly improve the neurological function in the animal after photochemical injury, therefore protecting against cerebral infarction in the SD rat model of photochemically induced focal cerebral ischemia.

It can be seen that, the mobility in the c-MET monoclonal antibody group is significantly better than that in the control group. The above results indicate that the c-MET monoclonal antibody can improve the clinical symptoms of cerebral infarction.

3) The Protective Effect of c-MET Humanized Chimeric Antibody on Cardiac Function in a Mouse Model for Heart Failure (MI Myocardial Infarction Model)

Mouse models for heart failure (MI myocardial infarction models) were established as described in Example 16 and grouped. Evaluation index: echocardiography was used to evaluate cardiac function indexes, and to observe the protective effect of the c-MET humanized chimeric antibody on the cardiac function in mouse MI myocardial infarction model.

Results: The echocardiographic evaluation results are shown in FIG. 26, in which FIG. 26-a shows the cardiac ejection fraction (EF), FIG. 26-b shows the left ventricular fraction shortening (FS), FIG. 26-c shows the left ventricular end-diastolic volume (EDV), and FIG. 26-d shows the left ventricular end-systolic volume (ESV). The injured group is injected with an equal amount of normal saline; there are 2 treatment groups, which are injected with c-MET humanized chimeric antibody at 1 mg/kg or 3 mg/kg, respectively. The results show that the EF in all the injured groups is less than 40%, indicating successful myocardial infarction modeling; after injection of 1 mg/kg/3d c-MET humanized chimeric antibody via tail vein, EF has a tendency to recover; after injection of 3 mg/kg/3d c-MET humanized chimeric antibody via tail vein, the recovery of EF is more obvious. The FS, EDV and ESV all have a similar trend. Therefore, it is shown that the c-MET humanized chimeric antibody has a protective effect on cardiac function in mouse MI myocardial infarction model.

The sequences used in the present invention:

```
(Upstream primer P1)
                                        SEQ ID NO: 1
TATACCGGTCGCCACCATGAAGGCCCCCGCTGTGCTTGCACCTG (Downstream primer P2)
                                        SEQ ID NO: 2
CGCGTCGACCTAGTGATGGTGATGATGGTGTGTGAAATTCTG
ATCTGGTTG ACATA (DNA sequence of human c-MET extracellular region)
                                        SEQ ID NO: 3
atgaaggcccccgctgtgcttgcacctggcatcctcgtgctcctgtttac cttggtgcagaggagcaatggggagtgtaaagaggcactagcaaagtccg agatgaatgtgaatatgaagtatcagcttcccaacttcaccgcggaaaca cccatccagaatgtcattctacatgagcatcacattttccttggtgccac taactacatttatgttttaaatgaggaagaccttcagaaggttgctgagt acaagactgggcctgtgctggaacacccagattgtttcccatgtcaggac tgcagcagcaaagccaatttatcaggaggtgtttggaaagataacatcaa catggctctagttgtcgacacctactatgatgatcaactcattagctgtg gcagcgtcaacagagggacctgccagcgacatgtctttccccacaatcat
```

-continued

```
actgctgacatacagtcggaggttcactgcatattctccccacagataga
agagcccagccagtgtcctgactgtgtggtgagcgccctgggagccaaag
tcctttcatctgtaaaggaccggttcatcaacttctttgtaggcaatacc
ataaattcttcttatttcccagatcatccattgcattcgatatcagtgag
aaggctaaaggaaacgaaagatggttttatgttttttgacggaccagtcct
acattgatgttttacctgagttcagagattcttaccccattaagtatgtc
catgcctttgaaagcaacaattttatttacttcttgacggtccaaaggga
aactctagatgctcagacttttcacacaagaataatcaggttctgttcca
taaactctggattgcattcctacatggaaatgcctctggagtgtattctc
acagaaaagagaaaaaagagatccacaaagaaggaagtgtttaatatact
tcaggctgcgtatgtcagcaagcctggggcccagcttgctagacaaatag
gagccagcctgaatgatgacattcttttcggggtgttcgcacaaaagcaag
ccagattctgccgaaccaatggatcgatctgccatgtgtgcattccctat
caaatatgtcaacgacttcttcaacaagatggtcaacaaaaacaatgtga
gatgtctccagcattttacggacccaatcatgagcactgctttaatagg
acacttctgagaaattcatcaggctgtgaagcgcgccgtgatgaatatcg
aacagagtttaccacagctttgcagcgcgttgacttattcatgggtcaat
tcagcgaagtcctcttaacatctatatccaccttcattaaaggagacctc
accatagctaatcttgggacatcagagggtcgcttcatgcaggttgtggt
ttctcgatcaggaccatcaaccctcatgtgaatttttctcctggactccc
atccagtgtctccagaagtgattgtggagcatacattaaaccaaaatggc
tacacactggttatcactgggaagaagatcacgaagatcccattgaatgg
cttgggctgcagacatttccagtcctgcagtcaatgcctctctgccccac
cctttgttcagtgtggctggtgccacgacaaatgtgtgcgatcggaggaa
tgcctgagcgggacatggactcaacagatctgtctgcctgcaatctacaa
ggttttcccaaatagtgcaccccttgaaggagggacaaggctgaccatat
gtggctgggactttggatttcggaggaataataaatttgatttaaagaaa
actagagttctccttggaaatgagagctgcaccttgactttaagtgagag
cacgatgaatacattgaaatgcacagttggtcctgccatgaataagcatt
tcaatatgtccataattatttcaaatggccacgggacaacacaatacagt
acattctcctatgtggatcctgtaataacaagtatttcgccgaaatacgg
tcctatggctggtggcactttacttactttaactggaaattacctaaaca
gtgggaattctagacacatttcaattggtggaaaaacatgtactttaaaa
agtgtgtcaaacagtattcttgaatgttatacccccagcccaaaccatttc
aactgagtttgagttaaattgaaaattgacttagccaaccgagagacaag
catcttcagttaccgtgaagatcccattgtctatgaaattcatccaacca
aatctttttattagtggtgggagcacaataacaggtgttgggaaaaacctg
aattcagttagtgtcccgagaatggtcataaatgtgcatgaagcaggaag
gaactttacagtggcatgtcaacatcgctctaattcagagataatctgtt
gtaccactccttccctgcaacagctgaatctgcaactcccctgaaaacc
aaagccttttttcagttagatgggatcctttccaaatactttgatctcatt
tatgtacataatcctgtgtttaagccttttgaaaagccagtgatgatctc
aatgggcaatgaaaatgtactggaaattaagggaaatgatattgaccctg
aagcagttaaaggtgaagtgttaaaagttggaaataagagctgtgagaat
atacacttacattctgaagccgttttatgcacggtccccaatgacctgct
gaaattgaacagcgagctaaatatagagtggaagcaagcaatttatcaac
cgtcatggaaaagtaatagttcaaccagatcagaatttcaca
```

(Amino acid sequence of extracellular region of human c-MET)
SEQ ID NO: 4

MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISGGSTITGVGKNLNSVSVPRMVINVHEAGRNFTVACQHRSNSEIIC

CTTPSLQQLNLQLPLKTKAFFMLDGILSKYFDLIYVHNPVFKPFEKPVMI

SMGNENVLEIKGNDIDPEAVKGEVLKVGNKSCENIHLHSEAVLCTVPNDL

LKLNSELNIEWKQAISSTVLGKVIVQPDQNFT (Heavy chain upstream primer)
SEQ ID NO: 5
SARGTRMAGCTGMAGSAGTC
wherein S is G or C; R is A or G; and M is A or C.

(Heavy chain downstream primer)
SEQ ID NO: 6
AATTTTCTTGTCCACCTTGGTGCTGCT (Light chain upstream primer)
SEQ ID NO: 7
GAYATTGTDMTSACMCARWCT
wherein Y is C or T; D is G or A or T; M is A or C; S is G or C; R is A or G; and W is A or T.

(Light chain downstream primer)
SEQ ID NO: 8
GGATACAGTTGGTGCAGCATCAGCCC (Amino acid sequence of c-MET antibody heavy chain CDR1)
SEQ ID NO: 9
GYSFTSYW (Amino acid sequence of c-MET antibody heavy chain CDR2)

SEQ ID NO: 10

IDPSDSES (Amino acid sequence of c-MET antibody heavy chain CDR3)

SEQ ID NO: 11

ARSGYHGTSYWYFDV (Amino acid sequence of c-MET antibody light chain CDR1)

SEQ ID NO: 12

KSLLHSDGITY (Amino acid sequence of c-MET antibody light chain CDR2)

SEQ ID NO: 13

QMS (Amino acid sequence of c-MET antibody light chain CDR3)

SEQ ID NO: 14

AQNLELPPT

---

The invention claimed is:

1. An antibody or functional fragment thereof capable of binding to c-MET, comprising a heavy chain and a light chain, wherein:
the heavy chain comprises a heavy chain variable region which comprises a CDR1 of SEQ ID NO: 9, a CDR2 of SEQ ID NO: 10, and a CDR3 of SEQ ID NO: 11, and
the light chain comprises a light chain variable region which comprises a CDR1 of SEQ ID NO: 12, a CDR2 of SEQ ID NO: 13, and a CDR3 of SEQ ID NO: 14.

2. A pharmaceutical composition comprising the antibody or functional fragment thereof according to claim 1, and a pharmaceutically acceptable carrier.

3. The pharmaceutical composition according claim 2, further comprising one or more pharmaceutically active compounds for treatment or prevention of a disease caused by vascular endothelial cell injury.

4. The pharmaceutical composition according to claim 2, further comprising an IRF5 inhibitor, paclitaxel, a lipid-lowering drug, or an angiogenesis inhibitor, or a combination thereof.

5. A method for treatment of an ischemic disease caused by vascular endothelial cell injury comprising administering to a subject in need thereof a therapeutically effective amount of a c-MET agonist antibody or functional fragment thereof according to claim 1 to reduce apoptosis of vascular endothelial cells.

6. The method according to claim 5, wherein the ischemic disease is cerebral infarction or myocardial infarction.

* * * * *